US010513502B2

(12) United States Patent
Ross-Medgaarden et al.

(10) Patent No.: US 10,513,502 B2
(45) Date of Patent: Dec. 24, 2019

(54) ALKYLENE OXIDE SEPARATION SYSTEM

(71) Applicant: Lyondell Chemical Technology, L.P., Houston, TX (US)

(72) Inventors: Elizabeth I. Ross-Medgaarden, Humble, TX (US); David W. Leyshon, Houston, TX (US); Karl P. Rufener, Humble, TX (US); Sunti Kongkitisupchai, Houston, TX (US); Richard J. Wolff, Friendswood, TX (US); Kimberly A. Petry, Friendswood, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 16/267,526

(22) Filed: Feb. 5, 2019

(65) Prior Publication Data
US 2019/0241534 A1 Aug. 8, 2019

Related U.S. Application Data

(60) Provisional application No. 62/626,338, filed on Feb. 5, 2018.

(51) Int. Cl.
*C07D 301/32* (2006.01)
*B01D 3/14* (2006.01)
*B01D 3/40* (2006.01)
*B01D 3/00* (2006.01)
*B01D 3/42* (2006.01)

(52) U.S. Cl.
CPC ............ *C07D 301/32* (2013.01); *B01D 3/008* (2013.01); *B01D 3/143* (2013.01); *B01D 3/40* (2013.01); *B01D 3/4227* (2013.01)

(58) Field of Classification Search
CPC ........ C07D 301/32; B01D 3/143; B01D 3/40; B01D 3/008; B01D 3/4227
See application file for complete search history.

(56) References Cited

U.S. PATENT DOCUMENTS

| 3,881,996 A | 5/1975 | Schmidt |
| 9,593,090 B2 | 3/2017 | Li et al. |
| 2015/0031905 A1 | 1/2015 | Li et al. |

OTHER PUBLICATIONS

The International Search Report and Written Opinion for PCT/US2019/016631 dated Apr. 12, 2019.

*Primary Examiner* — John M Mauro

(57) ABSTRACT

A propylene oxide separation system comprising a heavies distillation column configured to receive a crude propylene oxide stream and discharge a heavies purge bottoms comprising at least one impurity selected from acetone, methanol, aldehydes, aldehyde derivatives, water, heavy hydrocarbons comprising $C_5+$, or combinations thereof, and discharge a heavies distillation column overhead stream comprising a majority of the propylene oxide entering with the crude propylene oxide stream, and a first extractive distillation column configured to receive the heavies distillation column overhead stream and a first extraction solvent stream comprising a hydrocarbon solvent, and discharge a lights purge overhead comprising at least one impurity selected from aldehydes (e.g., acetaldehyde, formaldehyde, etc.) methyl formate, methanol, water, $C_3$ hydrocarbons, $C_4$ hydrocarbons, or combinations thereof, and discharge a rich solvent bottoms stream comprising a majority of the propylene oxide entering via the heavies distillation column overhead stream. A propylene oxide purification method is also provided.

20 Claims, 5 Drawing Sheets

ALKYLENE OXIDE SEPARATION SYSTEM

CROSS-REFERENCE TO RELATED APPLICATIONS

This application claims the benefit of priority to U.S. Provisional Patent Application No. 62/626,338 filed on Feb. 5, 2018, which is incorporated herein by reference in its entirety.

TECHNICAL FIELD

This disclosure relates to a system and process for the purification and recovery of propylene oxide which is formed via the epoxidation of propylene with hydroperoxides derived from oxidation of isobutane, ethyl benzene, cyclohexane, alkylates or cumene. More particularly, this disclosure relates to a system and method that provide for reduced amounts of propylene oxide in purge streams, and/or that facilitate the separation of impurities, such as the separation of light impurities in a first extractive distillation column, thereby improving propylene oxide yields, improving purity, or both. Still more particularly, this disclosure relates to a system and method for the purification and recovery of propylene oxide via a configuration which first removes select heavy impurities (a 'heavies-first' configuration).

BACKGROUND

Approximately 14.5 billion pounds of propylene oxide (PO) are produced per year. Propylene oxide has many uses. Between 60 and 70% of the propylene oxide is converted to polyether polyols for the production of polyurethane plastics. About 20% of propylene oxide is hydrolyzed into propylene glycol, via a process which is accelerated either by thermal reaction or by acid or base catalysis. Other major products are polypropylene glycol, propylene glycols ethers, and propylene carbonate. To produce these end products, propylene oxide substantially free of impurities is needed.

Methods of producing alkylene oxides including propylene oxide involve hydrochlorination, direct oxidation and epoxidation of its corresponding olefins by peroxide or hydroperoxide. The oxidates used in the epoxidation processes are derived from secondary or tertiary hydrocarbons by direct oxidation with molecular oxygen; hence, the oxidates contain oxygenate impurities and precursors. Additional oxygenate impurities are also generated in the step of epoxidation of olefins. Crude alkylene oxides, such as propylene oxide, particularly those produced via epoxidation with hydrocarbon oxidates, contain amounts of oxygenated impurities that are difficult to separate from alkylene oxides. The impurities may include water, acids, alcohols, aldehydes, alkanes, ketones and esters. A need exists for continued improvement of systems and methods for separating alkylene oxide from these impurity constituents of crude alkylene oxide streams.

Although the purity of crude propylene oxide, for example from a propylene oxide and tertiary butyl alcohol (PO/TBA) process, can be as high as 98.5%, the crude propylene oxide generally contains close-boiling impurities including, without limitation, one or more of water, methanol, methyl formate, formaldehyde, acetaldehyde, acetone, propionaldehyde, isobutylene oxide, aldehyde derivatives and $C_5$-$C_7$ hydrocarbons. To meet commercial grade product propylene oxide specification, the impurities are removed from the crude propylene oxide. Due to close-boiling points, these impurities are difficult to separate from the propylene oxide without using an elaborate propylene oxide refining or purification scheme that involves extractive distillation techniques.

Traditional propylene oxide purification includes the production of purge streams comprising propylene oxide (also referred to as 'slop propylene oxide cuts') that may equal from 18 to 22 weight percent of the propylene oxide entering the refining section in the crude propylene oxide. Such purge streams comprising propylene oxide are conventionally utilized to make propylene glycol (PG) to capture added value with reduced equipment and energy costs in the propylene oxide refining/purification section. Reduction of PO losses in purge stream can provide for greater overall recovery of product PO, which may be desirable relative to making PG.

It remains a challenge to recover a purified propylene oxide product containing low levels of impurities, such as aldehydes and alcohols, particularly for propylene oxide produced from a free-radical oxidation process, including for example tert-butyl hydroperoxide processes. Accordingly, improved systems and methods are needed for recovering propylene oxide, from effluent streams of various crude propylene oxide production methods, in a high state of purity without excessive loss of propylene oxide product.

SUMMARY

Herein disclosed is a propylene oxide separation system comprising: a heavies distillation column configured to receive a crude propylene oxide stream and discharge a heavies purge bottoms comprising at least one impurity selected from acetone, methanol, aldehydes, aldehyde derivatives, water, isobutylene oxide, heavy hydrocarbons comprising $C_5$+, or combinations thereof, and discharge a heavies distillation column overhead stream comprising a majority of the propylene oxide entering with the crude propylene oxide stream; and a first extractive distillation column configured to receive the heavies distillation column overhead stream and an extraction solvent stream comprising a hydrocarbon solvent, and discharge a lights purge overhead comprising at least one impurity selected from aldehydes, methyl formate, methanol, water, $C_3$ hydrocarbons, $C_4$ hydrocarbons, or combinations thereof, and discharge a rich solvent bottoms stream comprising a majority of the propylene oxide entering via the heavies distillation column overhead stream.

Also disclosed herein is a method comprising: (i) subjecting a crude propylene oxide stream to non-solvent distillation in a heavies distillation column to produce a heavies purge bottoms comprising at least one impurity selected from acetone, methanol, aldehydes, aldehyde derivatives, water, isobutylene oxide, heavy hydrocarbons comprising $C_5$+, or combinations thereof, and a heavies distillation column overhead stream comprising a majority of the propylene oxide entering in the crude propylene oxide stream; (ii) introducing the heavies distillation column overhead stream and an extractive distillation solvent stream comprising a hydrocarbon solvent into a first extractive distillation column to produce a lights purge overhead comprising at least one impurity selected from aldehydes, methyl formate, methanol, water, $C_3$ hydrocarbons, $C_4$ hydrocarbons, or combinations thereof, and a rich solvent bottoms stream comprising a majority of the propylene oxide entering via the heavies distillation column overhead stream; (iii) removing a side draw from the first extractive distillation column into a decanter apparatus, and therein allowing the formation of an aqueous phase purge comprising water and methanol, one or more glycols, or a combination thereof, and an organic phase stream comprising propylene oxide and the hydrocarbon solvent; and (iv) introducing the rich solvent bottoms stream from the first extractive distillation column into a first solvent stripper to produce a first solvent stripper overhead comprising a majority of the propylene oxide entering the first solvent stripper via the rich solvent bottoms stream and a first solvent stripper bottoms comprising lean hydrocarbon solvent.

Also disclosed herein is a method comprising: (i) subjecting a crude propylene oxide stream to non-solvent distillation in a heavies distillation column to produce a heavies purge bottoms comprising at least one impurity selected from acetone, methanol, aldehydes, aldehyde derivatives, water, isobutylene oxide, heavy hydrocarbons comprising $C_5+$, or combinations thereof, and a heavies distillation column overhead stream comprising a majority of the propylene oxide entering in the crude propylene oxide stream; (ii) introducing the heavies distillation column overhead stream and a first extractive distillation solvent stream comprising a hydrocarbon solvent into a first extractive distillation column to produce a lights purge overhead comprising at least one impurity selected from aldehydes, methyl formate, methanol, water, $C_3$ hydrocarbons, $C_4$ hydrocarbons, or combinations thereof, and a rich solvent bottoms stream comprising a majority of the propylene oxide entering via the heavies distillation column overhead stream; (iii) introducing at least a portion of the lights purge overhead from the first extractive distillation column into a decanting apparatus, and therein allowing the formation of an aqueous phase purge comprising water and methanol, one or more glycols, or a combination thereof, and an organic phase stream comprising propylene oxide and the hydrocarbon solvent; and (iv) introducing the rich solvent bottoms stream from the first extractive distillation column into a first solvent stripper to produce a first solvent stripper overhead comprising a majority of the propylene oxide entering the first solvent stripper via the rich solvent bottoms stream and a first solvent stripper bottoms comprising lean hydrocarbon solvent.

While multiple embodiments are disclosed, still other embodiments will become apparent to those skilled in the art from the following detailed description. As will be apparent, certain embodiments, as disclosed herein, are capable of modifications in various aspects without departing from the spirit and scope of the claims as presented herein. Accordingly, the detailed description herein below is to be regarded as illustrative in nature and not restrictive.

BRIEF DESCRIPTION OF THE DRAWING

The following figure illustrates an embodiment of the subject matter disclosed herein. The claimed subject matter may be understood by reference to the following description taken in conjunction with the accompanying figure, in which:

DETAILED DESCRIPTION

Overview

Figure 1:
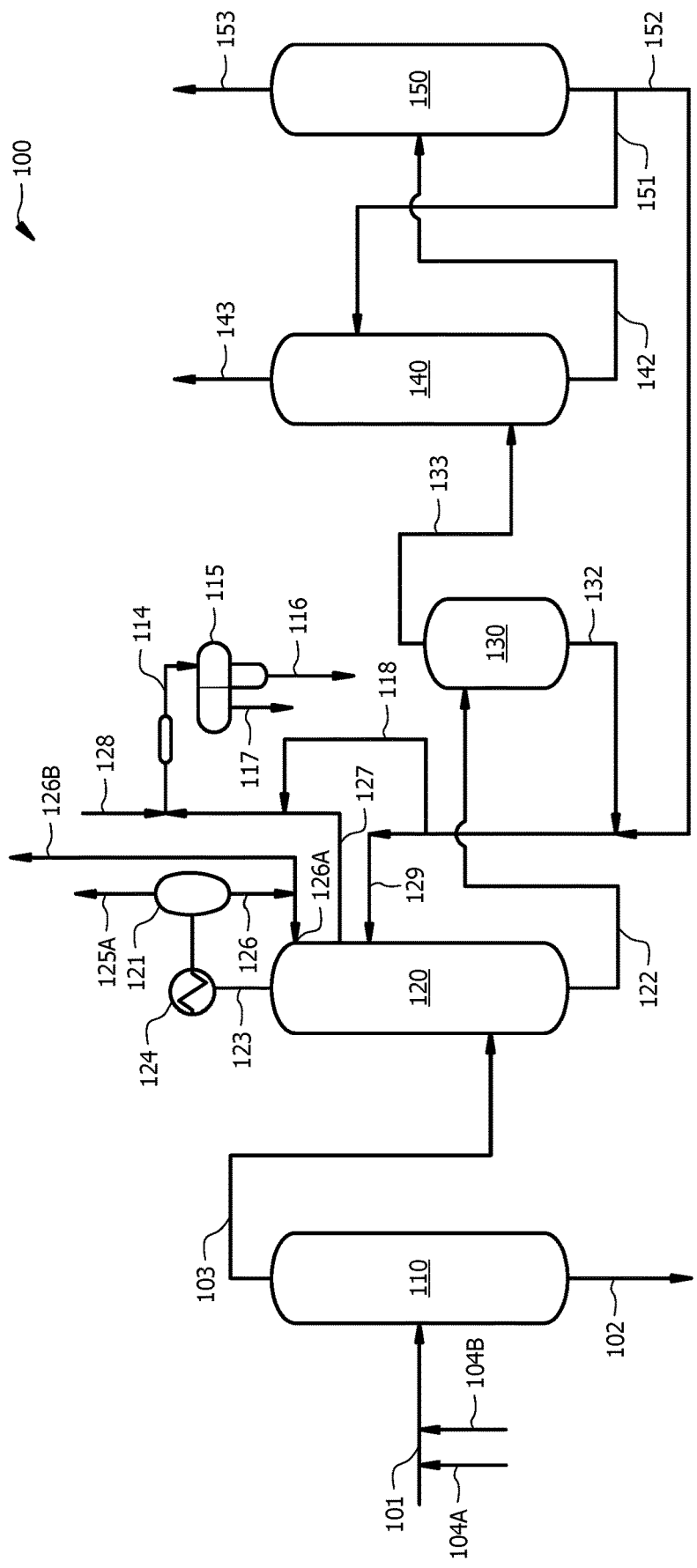
FIG. 1 is a schematic of a propylene oxide separation system 100 according to an embodiment of this disclosure.

The present disclosure may be understood more readily by reference to the following detailed description of various embodiments as well as to the examples included therein. As used herein, a 'majority' refers to greater than 50 weight percent.

This disclosure relates to a system and method for removing impurities from a crude propylene oxide stream. Propylene oxide (PO) is also known as epoxypropane, propylene epoxide, 1,2-propylene oxide, methyl oxirane, 1,2-epoxypropane, propene oxide, methyl ethylene oxide, and methylethylene oxide. PO may be produced in a PO/TBA process, in which PO and tert-butanol (TBA, also known as 2-methyl-2-propanol and tert-butanol) are formed. In such a PO/TBA process, isobutane (IB), also known as 2-methylpropane, can first be reacted with oxygen to form tert-butyl hydroperoxide (TBHP), also known as 2-methylpropane-2-peroxol. Subsequently, propylene (also known as propene) can be reacted with TBHP in the presence of a catalyst to form PO and TBA. Since this method produces both PO and TBA it is referred to herein as a PO/TBA process.

The crude propylene oxide purified via the herein-disclosed system and method may be produced via any process known in the art. In embodiments, a crude PO stream purified via the herein disclosed system and method is formed in a PO/TBA process. Production of a crude PO stream, for example from a PO/TBA process, is known to those skilled in the art.

The PO/TBA process can also yield a variety of unwanted side products or close-boiling impurities, which remain in the crude PO. Without wishing to be bound by theory, non-selective reactions can take place to produce the impurities. Such impurities can include, without limitation, acetone, alcohol(s) such as, without limitation, methanol, formaldehyde, propionaldehyde, water, formic acid, methyl formate, acetaldehyde, hydrocarbons, aldehydes, isobutylene oxide and the like. By way of example such non-selective reactions can include, without limitation, the production of acetone and methanol from TBHP; the production, in the presence of oxygen, of formaldehyde and water from methanol; the production, in the presence of oxygen, of formic acid from formaldehyde; the production of methyl formate and water from formic acid and methanol; the production of acetaldehyde and methanol from PO and water, or the like. Other reactions and impurities are possible.

The concentrations of these impurities that end up in a crude PO stream from a PO/TBA process can vary, and removal thereof is effected to provide a purified PO product. Herein disclosed are a system and method for removing impurities from such a crude PO stream. It has been unexpectedly discovered that removing a heavies cut upstream of extractive distillation enhances the effectiveness of the downstream extractive distillation. Without wishing to be limited by theory, the removal of aldehydes and/or aldehyde derivatives (e.g., formaldehyde and/or methylene glycol and/or dimethoxymethane) as a heavy (heavies) in the bottoms of an upstream heavies distillation column as disclosed herein prevents or minimizes the aldehydes and/or aldehyde derivatives from travelling downstream where the potential exists for decomposition of the heavies at higher temperatures to form close-boiling impurities (e.g., methanol, water, formaldehyde) that may end up in the purified PO product. Such aldehyde derivatives (e.g., formaldehyde derivatives) can form rapidly, but be unstable, making quantification thereof difficult.

A propylene oxide separation system and method (also referred to herein as a PO separation system or method or a propylene oxide purification system or method) will now be described with reference to FIG. 1, which is a schematic of a PO separation system 100 (also referred to as a 'PO purification system') according to an embodiment of this disclosure. For the sake of clarity, the respective reboiler and overhead condenser (including any reflux system) for each column (other than the condenser and associated reflux for first extractive distillation column 120) are not shown in FIG. 1. A system and method of this disclosure provide for separation of heavies from a crude PO stream via (non-solvent) distillation prior to (e.g., upstream of) further separation of impurities, such as, without limitation, extractive distillation to remove a lights purge stream, solvent stripping to provide a lean solvent for recycle, separation of a PO product via extractive distillation, separation of a hydrocarbon purge from a lean solvent stream which may be recycled, and the like. For example, PO separation system 100 comprises heavies distillation column 110 configured to separate heavies from a crude PO stream introduced thereto, thus providing a heavies purge bottoms and a heavies distillation column overhead stream comprising PO, said heavies distillation column 110 being located upstream from: an extractive distillation column (also referred to herein as a 'first' extractive distillation column as systems may further comprise a second extractive distillation column downstream therefrom) 120 configured for distillation of the heavies distillation column overhead stream, thus providing a lights purge overhead and a first extractive distillation column bottoms comprising PO; a solvent stripper 130 (also referred to herein as a 'first' solvent stripper as a second solvent stripper may be utilized downstream therefrom) configured to separate the first extractive distillation column bottoms comprising PO into a first solvent stripper bottoms comprising lean solvent and a first solvent stripper overhead comprising PO; a second extractive distillation column 140 configured to separate from the first solvent stripper overhead comprising PO an overhead PO product from a second extractive distillation column bottoms comprising rich solvent; and a second solvent stripper 150 configured to separate a hydrocarbon purge overhead from the second extractive distillation column bottoms comprising rich solvent to provide a second solvent stripper bottoms comprising lean solvent.

A crude PO stream is introduced into heavies distillation column 110 via crude PO inlet line 101. As noted hereinabove, in embodiments, the crude PO stream may be the product of the catalytic epoxidation of propylene with an organic hydroperoxide, for example the crude PO stream may be a PO/TBA process effluent stream. The PO/TBA process effluent stream may not have undergone any separation or distillation step to remove impurities prior to being fed to heavies distillation column 110. In embodiments, the crude PO stream can be the product of a PO/TBA process, as described hereinabove. The crude PO stream comprises primarily PO, and further comprises at least one impurity to be removed via the herein disclosed system and method. The crude PO stream may comprise a propylene oxide purity of less than or equal to 96, 97, 98, or 99 weight percent propylene oxide.

The crude PO stream 101 can include, but is not limited to, any combination of the impurities mentioned hereinabove along with the desired product, propylene oxide. As noted hereinabove, the impurity can comprise one or more impurities selected from methyl formate, acetone, alcohols (including, without limitation, methanol), isobutylene oxide, aldehydes and aldehyde derivatives such as methylene glycol (CAS 463-57-0) and/or methoxymethanol (CAS 4461-52-3), water, light hydrocarbons (e.g., hydrocarbons comprising three or more carbon atoms ($C_3$+), hydrocarbons comprising three carbon atoms ($C_3$), hydrocarbons comprising four carbon atoms ($C_4$), or a combination thereof), heavy hydrocarbons (e.g., hydrocarbons comprising five or more carbon atoms ($C_5$+), hydrocarbons comprising six or more carbon atoms ($C_6$+), hydrocarbons comprising five carbon atoms ($C_5$), hydrocarbons comprising six carbon atoms ($C_6$), or a combination thereof), and the like. In embodiments, the impurity comprises at least one selected from acetone, water, formaldehyde, methanol, formic acid, methyl formate, acetaldehyde, propionaldehyde, isobutylene oxide, formaldehyde derivatives, $C_5$-$C_7$ hydrocarbons (which may comprise primarily $C_6$ propylene dimers), and the like. Aldehydes can include formaldehyde, acetaldehyde, or the like. Aldehyde derivatives, such as formaldehyde derivatives, include heavier reaction products of the corresponding aldehyde. Such formaldehyde derivatives may include, without limitation, one or more hemiacetals, such as without limitation methylene glycol (CAS 463-57-0), hemiacetals (such as without limitation, methoxymethanol (CAS 4461-52-3), propylene glycol hemiformal, or the like), acetals (such as, without limitation, dimethoxymethane), paraformaldehyde, or combinations thereof.

Methyl formate can be present in the crude PO stream in an amount within a range having a lower limit and/or an upper limit, each expressed as a weight percentage of the total composition of the crude PO stream. The range can include or exclude the lower limit and/or the upper limit. The methyl formate lower limit and/or upper limit can be selected from 0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 2, 3, 4, 5, and 10 weight percent. For example, methyl formate can be present in an amount of greater than 0.02, 0.04, or 0.06 weight percent of the total composition of the crude PO stream.

One or more alcohols, such as, without limitation, methanol can be present in the crude PO stream in an amount within a range having a lower limit and/or an upper limit, each expressed as a weight percentage of the total composition of the crude PO stream. The range can include or exclude the lower limit and/or the upper limit. The one or more alcohols (e.g., methanol) lower limit and/or upper limit can be selected from 0, 0.001, 0.002, 0.003, 0.0031, 0.0032, 0.0033, 0.0034, 0.0035, 0.0036, 0.0037, 0.0038, 0.0039, 0.0139, 0.0239, 0.0339, 0.0439, 0.0539, 0.0639, 0.0739, 0.0839, 0.0939, 0.1039, 0.1049, 0.1059, 0.1069, 0.1079, 0.1089, 0.1099, 0.1109, 0.1119, 0.1129, 0.1139, 0.1149, 0.1159, 0.116, 0.1161, 0.1162, 0.1163, 0.1164, 0.1165, 0.1166, 0.1167, 0.1168, 0.1169, 0.117, 0.1171, 0.1172, 0.1173, 0.1174, 0.1175, 0.1176, 0.1177, 0.2177, 0.3177, 0.4177, 0.5177, 0.6177, 0.7177, 0.8177, 0.9177, 1, 2, 3, 4, 5, and 10 weight percent. For example, methanol can be present in an amount greater than 0.003, 0.03, 0.1172, or 0.3 weight percent of the total composition of the crude PO stream.

Acetaldehyde can be present in the crude PO stream in an amount within a range having a lower limit and/or an upper limit, each expressed as a weight percentage of the total composition of the crude PO stream. The range can include or exclude the lower limit and/or the upper limit. The acetaldehyde lower limit and/or upper limit can be selected from 0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 2, 3, 4, 5, and 10 weight percent. For example, acetaldehyde can be present in an amount of greater than 0.03, 0.01, or 0.005 weight percent of the total composition of the crude PO stream.

Formaldehyde can be present in the crude PO stream in an amount within a range having a lower limit and/or an upper limit, each expressed as a weight percentage of the total composition of the crude PO stream. The range can include or exclude the lower limit and/or the upper limit. The formaldehyde lower limit and/or upper limit can be selected from 0, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 2, 3, 4, 5, and 10 weight percent. For example, formaldehyde can be present in an amount of greater than 0.003, 0.005, 0.01, or 0.02 weight percent of the total composition of the crude PO stream.

Water can be present in the crude PO stream in an amount within a range having a lower limit and/or an upper limit, each expressed as a weight percentage of the total composition of the crude PO stream. The range can include or exclude the lower limit and/or the upper limit. The water lower limit and/or upper limit can be selected from 0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 2, 3, 4, 5, and 10 weight percent. For example, water can be present in an amount of greater than 0.16, 0.2, 0.3, or 0.8 weight percent of the total composition of the crude PO stream.

By way of example, the crude PO stream may comprise (each expressed as an average weight percentage of the total composition of the crude PO stream): from 0.05 to 1.5, from 0.02 to 1.0, or from 0.01 to 0.07 weight percent methyl formate (MeF), from 0.05 to 1.5, from 0.1 to 1.0, or from 0.2 to 0.8 weight percent methanol (MeOH), from 0.001 to 0.03, from 0.003 to 0.02, or from 0.004 to 0.04 weight percent aldehydes and/or aldehyde derivatives, from 0.001 to 0.05, from 0.003 to 0.03, or from 0.006 to 0.04 weight percent acetaldehyde (AA), from 0.001 to 0.04, from 0.002 to 0.03, or from 0.003 to 0.02 weight percent formaldehyde (FA), from 0.05 to 1.5, from 0.1 to 1.0, or from 0.2 to 0.8 weight percent water, from 0.001 to 0.5, from 0.002 to 0.4, or from 0.01 to 0.3 weight percent hydrocarbons, from 0.01 to 0.1, from 0.02 to 0.08, or from 0.03 to 0.06 weight percent light hydrocarbons ($C_3+$ hydrocarbons, $C_3$ hydrocarbons, $C_4$ hydrocarbons, or a combination thereof), from 0.01 to 0.2, from 0.02 to 0.15, or from 0.03 to 0.1 weight percent heavy hydrocarbons ($C_5+$, $C_6+$, $C_5$, $C_6$, or a combination thereof), or a combination thereof.

Distillation of the crude PO stream within heavies distillation column 110 produces a heavies purge bottoms which is removed from heavies distillation column 110 via heavies distillation column bottoms line 102 and a heavies distillation column overhead stream which is removed from heavies distillation column 110 via heavies distillation column overhead line 103. The heavies distillation column overhead stream comprises a majority of the PO introduced into heavies distillation column 110 via crude PO inlet line 101.

Heavies distillation column 110 can be a non-solvent distillation column, and can be made of any suitable material, including but not limited to carbon steel, stainless steel, fiberglass reinforced polymer (FRP), nickel alloys, and so on. Heavies distillation column 110 can include any suitable number of theoretical stages or trays, for example, about 30, 60, or 100 theoretical stages. In embodiments, the crude PO stream can be introduced to heavies distillation column 110 at least 15, 20, or 25% up from the bottom. In embodiment, the crude PO stream can be introduced into the heavies distillation column 110 at or between any stage 5 to 20, inclusive, counting from the bottom thereof. A packing material can be employed in the heavies distillation column to enhance vapor-liquid contact. Packing materials can be made from any suitable material including, without limitation, glass, metal, plastic, or ceramic. The packing can be structured or random. Trays such as sieve trays, bubble cap trays or valve trays can also be used.

In embodiments, heavies distillation column 110 may be operated at temperatures in the range of from 30 to 150 degrees Celsius (° C.), from 35° C. to 125° C. or from 40° C. to 100° C. In embodiments, heavies distillation column 110 may be operated at pressures in the range of from 0 psig to 60 psig (from 0 kPa gauge to 414 kPa gauge), from 0 psig to 45 psig (from 0 kPa gauge to 311 kPa gauge), or from 0 psig to 25 psig (from 0 kPa gauge to 138 kPa gauge).

Without wishing to be bound by theory, a PO separation system and method of this disclosure comprising upfront heavies removal via heavies distillation column 110 may provide for enhanced removal of at least one aldehyde and/or methanol because of the removal effected via the heavies removal of hemiacetals and/or acetals. An aldehyde (having formula $R_1CHO$), such as formaldehyde, can react with an alcohol (having formula $R_2OH$), such as, without limitation, methanol, to form a hemiacetal (having formula $R_1HC(OH)OR_2$, where $R_1$ and $R_2$ can be, for example, hydrogen, or a $C_1$ to $C_{10}$ alkyl. Examples of hemiacetals are methylene glycol (CAS463-57-0) and methoxy methanol (CAS 4461-52-3) or other compounds produced via aldehyde/alcohol combination. Formation of an acetal can occur when the hydroxyl group of a hemiacetal becomes protonated and is lost as water. In solvent systems, both formaldehyde and methanol would be lights by themselves, but hemiacetals and acetals formed therefrom can be heavy.

Subsequently, if not removed via the heavies purge bottoms from heavies distillation column 110 or the lights purge from first extractive distillation column 120, these addition products can travel downstream (with the PO in the rich solvent bottoms stream in first extractive distillation bottoms line 122 discussed herein below) where temperatures may increase and the reaction reverse. When the reaction reverses, such aldehydes and/or alcohols can become undesirably tracked with the PO product.

As a higher amount of methanol and/or water in the crude PO stream may provide for enhanced removal of aldehydes and/or aldehyde derivatives (such as, without limitation, formaldehyde derivatives) via heavies distillation column 110, and a purer product PO stream (e.g., in an overhead PO product stream extracted from second extractive distillation column 140 via second extractive distillation column overhead line 143, discussed further hereinbelow), a line 104A may be configured for the introduction of methanol into the crude PO stream, a line 104B may be configured for the introduction of water into the crude PO stream, or both. In embodiments, water and methanol are present in the feed to heavies distillation column 110 at the levels provided hereinabove. Water, methanol, or both may be added to the crude PO stream from a PO/TBA process to provide a desired level of methanol and/or water within heavies distillation column 110. In embodiments, an amount of methanol and/or water in the crude PO stream introduced into heavies distillation column 110 may be adjusted (via methanol addition via line 104A and/or water addition via line 104B) to a desired level based on a total aldehyde concentration in the heavies distillation column overhead removed via heavies distillation column overhead line 103. In embodiments, the desired level of methanol in the feed to heavies distillation column 110 (i.e., the amount of methanol in the crude PO stream or the amount of methanol in the crude PO stream combined with the amount of methanol introduced via inlet line 104A) comprises from 0.05 to 0.7, from 0.1 to 0.5, or from 0.2 to 0.4 weight percent methanol. In embodiments, the desired level of water in the feed to heavies distillation column 110 (i.e., the amount of water in the crude PO stream or the amount of water in the crude PO stream combined with the amount of water introduced via inlet line 104B) comprises from 0.1 to 1.0, from 0.2 to 0.8, or from 0.3 to 0.6 weight percent water. Although methanol is specifically noted herein, other alcohol(s) may be employed in an alcohol inlet line 104A and/or may be present in the crude PO stream introduced via crude PO inlet line 101, or elsewhere methanol is mentioned herein.

The heavies purge bottoms removed via heavies purge bottoms line 102 may comprise one or more heavies impurities selected from acetone, methanol, aldehydes and aldehyde derivatives, water, heavy hydrocarbons (i.e., $C_5+$, $C_6+$, $C_5$, $C_6$ or a combination thereof), acrolein, propionaldehyde (PA), isobutylene oxide (IBO), formic acid, or combinations thereof. In embodiments, the heavies purge bottoms comprise at least one selected from acetone, methanol, aldehydes and aldehyde derivatives, water, heavy hydrocarbons, or combinations thereof. The aldehydes and aldehyde derivatives may comprise formaldehyde and/or formaldehyde derivatives. In embodiments, the heavies purge bottoms removed from heavies distillation column 110 via heavies purge bottoms line 102 comprises at least 10, 15, 20, 25, or 30 weight percent of the methanol introduced with the crude PO stream via crude PO inlet line 101. In embodiments, the heavies purge bottoms removed from heavies distillation column 110 via heavies purge bottoms line 102 comprises at least 40, 45, 50, 55, or 60 weight percent of the water introduced with the crude PO stream via crude PO inlet line 101.

The heavies distillation column overhead stream removed via heavies distillation column overhead line 103 comprises a majority of the PO introduced into heavies distillation column 110 with the crude PO stream, and may further comprise (each expressed as an average weight percentage of the total composition of the heavies distillation column overhead stream): from 0.02 to 0.08, from 0.03 to 0.07, or from 0.04 to 0.06 weight percent methyl formate (MeF), from 0.1 to 0.5, from 0.2 to 0.4, or from 0.25 to 0.35 weight percent methanol (MeOH), from 0.005 to 0.05, from 0.01 to 0.04, or from 0.015 to 0.03 weight percent aldehydes and/or aldehyde derivatives, from 0.002 to 0.04, from 0.003 to 0.03, or from 0.004 to 0.02 weight percent acetaldehyde (AA), from 0.0 to 0.01, from 0.0 to 0.005, or from 0.0 to 0.0001 weight percent formaldehyde (FA), from 0.05 to 0.5, from 0.03 to 0.4, or from 0.01 to 0.3 weight percent water, from 0.01 to 0.2, from 0.03 to 0.5, or from 0.05 to 0.8 weight percent hydrocarbons, from 0.005 to 0.08, from 0.015 to 0.1, or from 0.02 to 0.3 weight percent light hydrocarbons ($C_3+$ hydrocarbons, $C_3$ hydrocarbons, $C_4$ hydrocarbons, or a combination thereof), from 0.001 to 0.02, from 0.002 to 0.01, or from 0.003 to 0.008 weight percent heavy hydrocarbons ($C_5+$ hydrocarbons, $C_6+$ hydrocarbons, $C_5$ hydrocarbons, $C_6$ hydrocarbons, or a combination thereof), or a combination thereof.

The heavies distillation column overhead stream is introduced via heavies distillation column overhead line 103 into an extractive distillation column 120 (which, as noted hereinabove, may be referred to as a 'first' extractive distillation column in systems further comprising a second extractive distillation column downstream therefrom) configured for the removal of a first extractive distillation column overhead comprising a majority of the impurities (for example, methanol) introduced thereto and a first extractive distillation column bottoms comprising a majority of the PO introduced into first extractive distillation column 120.

First extractive distillation column 120 is operable to separate, via distillation with an extraction solvent introduced thereto via first extractive distillation column extraction solvent inlet line 129, a first extractive distillation column overhead or 'lights purge' comprising at least one impurity from a stream comprising a majority of the PO introduced into the first extractive distillation column via heavies distillation column overhead line 103. In embodiments, the lean extraction solvent introduced via first extractive distillation column extraction solvent inlet line 129, as well as the lean extraction solvent introduced into second extractive distillation column 140 via second extractive distillation column extraction solvent inlet line 151 (described hereinbelow), the rich solvent, and the lean solvent referred to hereinbelow comprise a hydrocarbon solvent comprising one or more $C_6$-$C_{20}$ paraffin, or one or more $C_6$-$C_{10}$ paraffin. For example, in embodiments, the hydrocarbon solvent comprises primarily octane.

First extractive distillation column 120 can be made of any suitable material, including but not limited to carbon steel, stainless steel, fiberglass reinforced polymer (FRP), nickel alloys, and so on. First extractive distillation column 120 can include any suitable number of trays or theoretical stages, for example, about 25, 30, 35, 40 or 45 theoretical stages. In embodiments, the heavies distillation column overhead stream from heavies distillation column 110 may be introduced into first extractive distillation column 120 via heavies distillation column overhead line 103 at a position from 45 to 85, from about 50 to 80, from 55 to 75, or at least 45, 50, or 55% of the way up from the bottom of first extractive distillation column 120. A packing material can be employed in the first extractive distillation column to enhance vapor-liquid contact. Packing materials can be made from any suitable material known to those of skill in the art including, without limitation, glass, metal, plastic, or ceramic. The packing can be structured or random. Trays such as sieve trays, bubble cap trays or valve trays can also be used.

In embodiments, first extractive distillation column 120 can be operated at temperatures in the range of from 50 to 150 degrees Celsius (° C.), from 40° C. to 175° C., or from 30° C. to 200° C. In embodiments, first extractive distillation column 120 can be operated at pressures in the range of from 0 psig to 60 psig (from 0 kPa gauge to 414 kPa gauge), from 10 psig to 50 psig (from 69 kPa gauge to 350 kPa gauge), or from 15 psig to 45 psig (from 104 kPa gauge to 311 kPa gauge). In embodiments, first extractive distillation column 120 can be an extractive distillation column as described in U.S. Pat. No. 9,593,090, the disclosure of which is hereby incorporated herein by reference in its entirety for purposes not contrary to this disclosure. However, as described further hereinbelow, utilization of heavies distillation upstream of first extractive distillation column 120 may enable operation of first extractive distillation column 120 at lower operating conditions than those described in U.S. Pat. No. 9,593,090.

The first extractive distillation column overhead or 'lights purge' includes at least one impurity and is removed from first extractive distillation column 120 via a first extractive distillation column overhead line 123. A cooler 124 may be utilized to reduce the temperature of the first extractive distillation column overhead introduced thereto from first extractive distillation column overhead line 123. In embodiments, cooler 124 is operated to reduce the temperature of the first extractive distillation column overhead from a temperature in the range of from 50° C. to 65° C., from 70° C. to 90° C., or from 35° C. to 50° C. to a temperature in the range of from 40° C. to 50° C., from 45° C. to 70° C., or from 25° C. to 35° C.

Knock out (K/O) 121 may be utilized to separate a gas comprising uncondensed component(s) from a liquid comprising condensed component(s). An uncondensed component or 'vapor purge' outlet line 125A may be operable to remove the gas comprising uncondensed component(s) from K/O 121, and a condensed component outlet line 126 may be operable to remove a liquid comprising condensed component(s) from K/O 121. Components in the overhead stream in first extractive distillation column overhead line 123 entering K/O 121 that are not condensed can be purged from PO separation system 100 via vapor purge line 125A. These non-condensed components in vapor purge line 125A may be sent to another process, discharged as waste, and the like. If desired, the non-condensed components in vapor purge line 125A may be subjected to further local processing, such as in an additional condenser operating at lower temperature than that of K/O 121, and so forth. In embodiments, the non-condensed components in vapor purge line 125A may include acetaldehyde, methyl formate, and/or other undesired impurities.

A portion of the condensate from K/O 121 may be returned as reflux to first extractive distillation column 120 via first extractive distillation column overhead reflux line 126A, and a portion of the condensate from K/O 121 may be removed from the system as a liquid lights purge via liquid lights purge line 126B.

The lights purge removed via first extractive distillation column overhead line 123, vapor lights purge 125A, and/or liquid lights purge line 126B may comprise one or more impurities selected from aldehydes (for example, acetaldehyde (AA), formaldehyde, etc.), methyl formate (MF), methanol (MeOH), water, $C_3$ (i.e., hydrocarbons comprising three carbons), $C_4$ (i.e., hydrocarbons comprising four carbons), or a combination thereof.

In embodiments, first extractive distillation column 120 is further configured to discharge a side draw. For example, in the embodiment of FIG. 1, first extractive distillation column 120 is configured with a side draw line 127, whereby a liquid side draw can be removed from first extractive distillation column 120. The liquid side draw in line 127 from first extractive distillation column 120 can comprise PO, water, methanol, acetaldehyde, glycols, and/or other impurities and can be introduced to a decanter 115. Decanter 115 can facilitate the removal of water, glycol(s) and other water-soluble impurities from first extractive distillation column 120 via an aqueous phase purge. For example, the liquid side draw removed via liquid side draw line 127 can be combined with water in water inlet line 128 and with solvent (e.g., lean solvent), for example via decanter lean solvent line 118 (which may be fluidly connected with first solvent stripper 130, second solvent stripper 150, or both, as described in more detail hereinbelow), and introduced via decanter feed line 114 into decanter 115.

Decanter 115 is configured for separation of an aqueous phase from an organic phase. Although referred to as a 'decanter', in embodiments, decanter 115 comprises one or more of a mixer, a coalescer and a decanter. The mixer may comprise an orifice mixer, a static mixer, or the like. Decanter 115 may comprise a decanter and/or water wash system as described in U.S. Pat. No. 9,593,090, or any other suitable water wash and decanting system, and may be referred to as a 'water wash decanter'. An aqueous phase purge with a high concentration of impurities can be purged from decanter 115 via aqueous phase purge outlet line 116. The aqueous purge may comprise, for example, water, methanol, one or more glycols, methyl formate, aldehydes (for example, acetaldehyde, formaldehyde, etc.), aldehyde derivatives, other aqueous phase impurities, or a combination thereof. The aqueous phase purge may comprise a majority weight percent of the methanol and the water fed to decanter 115 in decanter feed line 114. As noted hereinabove, and without wishing to be limited by theory, a source of glycol impurities in PO separation system 100 may be various solvents therein that deteriorate over time in the presence of water and propylene oxide, for instance, to form glycols. By removing the impurities (for example, water and propylene glycol), the hydrocarbon solvent performance in PO separation system 100 may be maintained. In embodiments, the aqueous phase purge comprises from 10 to 50, from 15 to 45, or from 20 to 40 weight percent methanol. In embodiments, the aqueous phase purge comprises from 0.1 to 5.0, from 0.2 to 2.5, or from 0.3 to 1.0 weight percent of one or more glycols.

The organic phase can be removed from decanter 115 via organic phase outlet line 117. The organic phase may comprise, for example, extraction solvent, propylene oxide, or a combination thereof. In embodiments, the organic phase comprises from 50 to 95, from 60 to 90, or from 70 to 90 weight percent extraction solvent. In embodiments, the organic phase comprises from 5 to 30, from 7 to 25, or from 10 to 20 weight percent propylene oxide. The organic phase in organic phase outlet line 117 and/or first extractive distillation column solvent inlet line 129 can include an amount of aqueous phase within a range having a lower limit and/or an upper limit, each expressed as weight percentages. The range can include or exclude the lower limit and/or the upper limit. The lower limit and/or upper limit for the amount of the aqueous phase in the organic phase can be selected from 0, 0.01, 0.02, 0.03, 0.04, 0.05, 0.1, 0.2, 0.3, 0.4, 0.5, 0.7, 1, 2, 3, 4, 5, 6, 7, 8, 9, and 10 weight percent. For example, less than 0.1% of the aqueous phase can be present in the organic phase effluent of the wash or less than 10% of the aqueous phase can be present in the organic phase effluent of the wash.

The water wash in decanter 115 can be carried out by combining the liquid side draw in side draw line 127 (comprising propylene oxide and impurities) with water and solvent (e.g., hydrocarbon solvent). The water supplied via water inlet line 128 can be used to remove impurities from propylene oxide. The water introduced via water inlet line 128 can comprise tap water, treated water, demineralized water, deionized water, recovered process water, or a combination thereof. The solvent supplied via decanter lean solvent line 118 can be used to reduce propylene oxide loss into the water phase. Adequate mixing can promote impurity removal. Adequate coalescing, and enough residence time in decanter 115 can also help reduce entrainment of the aqueous phase in the organic phase effluent. It is noted that other configurations of first extractive distillation column 120 and decanter 115 are contemplated to form and discharge the aqueous phase purge. For example, other configurations are taught in U.S. Pat. No. 9,593,090.

First extractive distillation column extraction solvent inlet line 129 is configured to introduce extraction solvent into first extractive distillation column 120 at a point in the range of from 65 to 95, from 65 to 90, from 70 to 90, or at least 60, 65, or 70% up from the bottom of first extractive distillation column 120. In embodiments, solvents recovered from decanter 115 in the organic phase can be recycled to first extractive distillation column 120, such that PO and/or hydrocarbon solvent therein can be recovered or reused.

The removal of lights and aqueous purges via first extractive distillation column 120 and decanter 115 is effective in removing various light impurities, such as, without limitation, methyl formate, formaldehyde, acetaldehyde, aldehyde derivatives, water, and methanol. This can help keep hemiacetal and/or acetal formation low in first extractive distillation column 120. As noted herein hereinabove, hemiacetal and acetal could undesirably enter into the rich solvent bottoms in first extractive distillation column bottoms line 122 and later breakdown in downstream columns into aldehydes and alcohols to contaminate the propylene oxide product, and removal of hemiacetals, acetals, and/or precursors thereof via heavies distillation column 110, first extractive distillation column 120, and/or decanter 115 may minimize the presence of impurities in the purified PO product (e.g., the overhead PO product stream removed from second extractive distillation column 140 via second extractive distillation column overhead line 143).

Impurities removed via first extractive distillation column 120 can include methyl formate, formaldehyde, acetaldehyde, methanol, water, or combinations thereof. A majority of the impurities in the lights purge overhead removed from first extractive distillation column 120 via first extractive distillation column overhead line 123 can be removed through a combination of the vapor purge gas in uncondensed component outlet line 125A, the liquid lights purge in liquid lights purge line 126B, and the aqueous purge in aqueous phase purge outlet line 116 from decanter 115.

A solvent stripper 130 (which may be referred to herein as a 'first' solvent stripper when a second solvent stripper 150 is utilized downstream therefrom) may be utilized to separate hydrocarbon solvent from the rich solvent bottoms stream removed from first extractive distillation column 120 and introduced into first solvent stripper 130 via first extractive distillation column bottoms line 122.

First solvent stripper 130 may comprise a trayed stripper or a stripper containing packing. First solvent stripper 130 can be made of any suitable material, including but not limited to stainless steel, carbon steel, fiberglass reinforced polymer (FRP), nickel alloys, and so on. First solvent stripper 130 can include any suitable number of trays or theoretical stages, for example, about 0, 5, 10, or 15 theoretical stages. The rich solvent bottoms in first extractive distillation column bottoms line 122 can be introduced into first solvent stripper 130 at the top of the tray section or the packing section. A packing material can be employed in first solvent stripper 130 to enhance vapor-liquid contact. Packing materials can be made from any suitable material, including, without limitation, glass, metal, plastic, and ceramic. If packing is used, it can be structured or random, and the like. If trays are used, the trays can be sieve trays, bubble cap trays or valve trays, and so on.

In embodiments, first solvent stripper 130 can be operated at temperatures in the range of from 80 to 200 degrees Celsius (° C.), from 90° C. to 180° C., or from 100° C. to 175° C. In embodiments, first solvent stripper 130 can be operated at pressures in the range of from 0 psig to 40 psig (from 0 kPa gauge to 276 kPa gauge), from 10 psig to 40 psig (from 69 kPa gauge to 276 kPa gauge), from 15 psig to 30 psig (from 104 kPa gauge to 210 kPa gauge), or from 17 psig to 35 psig (from 118 kPa gauge to 244 kPa gauge).

A first solvent stripper overhead line 133 is configured for removal of a first solvent stripper overhead comprising a majority of the propylene oxide entering with the rich solvent bottoms stream, and a first solvent stripper bottoms line 132 is configured for removal of a first solvent stripper bottoms comprising lean solvent. First solvent stripper 130 may be fluidly connected with first extractive distillation column 120 (for example via first solvent stripper bottoms line 132 and first extractive distillation column extraction solvent inlet line 129), such that at least a portion of the lean solvent separated from the rich solvent bottoms stream in first solvent stripper 130 can be introduced into first extractive distillation column 120 as extraction solvent. Alternatively, or additionally, first solvent stripper 130 may be fluidly connected with decanter 115 (for example via a combination of first solvent stripper bottoms line 132, first extractive distillation column extraction solvent inlet line 129, and/or decanter lean solvent inlet line 118), such that at least a portion of the lean solvent separated from the rich solvent bottoms stream in first solvent stripper 130 can be introduced into decanter 115.

A second extractive distillation column 140 may be configured to separate the first solvent stripper overhead into a second extractive distillation column overhead comprising a PO product stream comprising a majority of the PO introduced into second extractive distillation column 140 via the first solvent stripper overhead and a second extractive distillation column bottoms comprising rich solvent. Second extractive distillation column 140 is operable to separate, via distillation with an extraction solvent, a second extractive distillation column or 'PO product' overhead comprising a majority of the PO introduced into second extractive distillation column 140 via first solvent stripper overhead line 133 from a second extractive distillation column bottoms comprising rich solvent. The second extractive distillation column overhead comprising PO product is removed from second extractive distillation column 140 via a second extractive distillation column overhead line 143. A second extractive distillation column bottoms line 142 can be configured to remove the second extractive distillation column bottoms comprising rich solvent from second extractive distillation column 140. Extraction solvent can be introduced into second extractive distillation column 140 via a second extractive distillation column extraction solvent inlet line 151, which may be fluidly connected with a second solvent stripper 150, as described further hereinbelow. The extraction solvent may be introduced into second extractive distillation column 140 at a point 50 to 90%, 60-90%, or 50 to 85% up from the bottom.

Second extractive distillation column 140 can be made of any suitable material, including but not limited to carbon steel, stainless steel, fiberglass reinforced polymer (FRP), nickel alloys, and so on. Second extractive distillation column 140 can include any suitable number of trays or theoretical stages, for example, about 50, 40, or 30 theoretical stages. In embodiments, the first solvent stripper overhead in first solvent stripper overhead line 133 from first solvent stripper 130 may be introduced into second extractive distillation column 140 at a point a minimum of 15, 20, or 25% up from the bottom thereof. A packing material can be employed in second extractive distillation column 140 to enhance vapor-liquid contact. Packing materials can be made from any suitable material including, without limitation, glass, metal, plastic, or ceramic. The packing can be structured or random. Trays such as sieve trays, bubble cap trays or valve trays can also be used.

In embodiments, second extractive distillation column 140 can be operated at temperatures in the range of from 30 to 250 degrees Celsius (° C.), from 40° C. to 200° C., or from 45° C. to 175° C. In embodiments, second extractive distillation column 140 can be operated at pressures in the range of from 0 psig to 60 psig (from 0 kPa gauge to 414 kPa gauge), from 5 psig to 50 psig (from 35 kPa gauge to 350 kPa gauge), or from 10 psig to 40 psig (from 69 kPa gauge to 276 kPa gauge).

The PO product removed from second extractive distillation column 140 via second extractive distillation column overhead line 143 may comprise less than 0.010, 0.005, 0.004, 0.003, 0.002 or 0.001 weight percent (less than 100, 50, 40, 30, 20 or 10 ppm) methanol, less than 0.010, 0.005, 0.004, 0.003, 0.002, 0.001 or 0.0005 weight percent (less than 100, 50, 40, 30, 20, 10 or 5 ppm) methyl formate, less than 0.025, 0.010, or 0.005 weight percent (less than 250, 100, or 50 ppm) water, less than 0.005, 0.002, or 0.001 weight percent (less than 50, 20, or 10 ppm) acetaldehyde, less than 0.001, 0.0005, or 0.0001 weight percent (less than 10, 5, or 1 ppm) formaldehyde and/or aldehyde derivatives, or a combination thereof. The propylene oxide purity of the overhead PO product in second extractive distillation column overhead line 143 (i.e., the distillate of second extractive distillation column 140) may be greater than or equal to 99.0, 99.9, 99.98, or 99.99 weight percent propylene oxide. Such a purified PO (e.g., having a PO purity of greater than or equal to 99.0, 99.9, 99.98, or 99.99 weight percent propylene oxide) may be referred to herein as a 'pure' PO. A PO separation system 100 and method of this disclosure comprising upfront heavies removal may give a relatively high yield of greater than or equal to 90, 95, or 98 weight percent PO recovery from the crude PO stream in the crude PO inlet line 101 into the PO product in the condensed second extractive distillation column overhead in second extractive distillation column overhead line 143 sent as distillate product.

Second extractive distillation column bottoms line 142 can be configured to introduce the second extractive distillation column bottoms comprising rich solvent into a second solvent stripper 150. Second solvent stripper 150 may comprise a distillation column. Second solvent stripper 150 can be made of any suitable material, including but not limited to stainless steel, carbon steel, fiberglass reinforced polymer (FRP), nickel alloys, and so on. Second solvent stripper 150 can include any suitable number of theoretical stages, for example, about 30, 25, 20, 15, or 10 theoretical stages. The second extractive distillation column bottoms comprising rich solvent in second extractive distillation column bottoms line 142 can be introduced into second solvent stripper 150 at a point 60% to 95%, 65% to 90%, or 70% to 85% up from the bottom thereof. A packing material can be employed in second solvent stripper 150 to enhance vapor-liquid contact. Packing materials can be made from any suitable material, including, without limitation, glass, metal, plastic, and ceramic. If packing is used, it can be structured or random, and the like. If trays are used, the trays can be sieve trays, bubble cap trays or valve trays, and so on.

In embodiments, second solvent stripper 150 can be operated at temperatures in the range of from 40 to 200 degrees Celsius (° C.), from 45° C. to 190° C., or from 45° C. to 180° C. In embodiments, second solvent stripper 150 can be operated at pressures in the range of from 5 psig to 45 psig (from 35 kPa gauge to 311 kPa gauge), from 5 psig to 30 psig (from 35 kPa gauge to 207 kPa gauge), or from 15 psig to 45 psig (from 104 kPa gauge to 311 kPa gauge).

A second solvent stripper overhead line 153 can be configured for the removal of a light hydrocarbon purge stream comprising hydrocarbon impurities, such as, but not limited to, $C_5$, $C_6$ and/or $C_7$ hydrocarbons. In embodiments, the light hydrocarbon purge in second solvent stripper overhead line 153 comprises primarily $C_6$, primarily $C_7$, or a combination thereof. For example, such hydrocarbon impurities include, without limitation, 2-methyl pentane, propylene glycol methyl ether and various $C_5+$ hydrocarbons. (Although referred to as a light hydrocarbon purge, the hydrocarbons in the light hydrocarbon purge may be considered 'heavy' hydrocarbons relative to the hydrocarbons (primarily $C_3$ and $C_4$) removed via liquid lights purge line 126B.) A second solvent stripper bottoms line 152 can be configured for the removal of a second solvent stripper bottoms comprising lean solvent (e.g., primarily $C_8$-$C_{20}$ hydrocarbon(s), for example, primarily octane). In embodiment, at least a portion of the lean solvent in the second solvent stripper bottoms can be introduced via second extractive distillation column extraction solvent inlet line 151 into second extractive distillation column 140, as discussed hereinabove. In embodiments, at least a portion of the lean solvent in the second solvent stripper bottoms can be introduced via second solvent stripper bottoms line 152 into first extractive distillation column 120 via first extractive distillation column extraction solvent inlet line 129. In embodiments, at least a portion of the lean solvent in the second solvent stripper bottoms can be introduced via second solvent stripper bottoms line 152 into decanter 115 via first extractive distillation column extraction solvent inlet line 129, water wash decanter lean solvent line 118 and/or decanter feed line 114.

Figure 2:
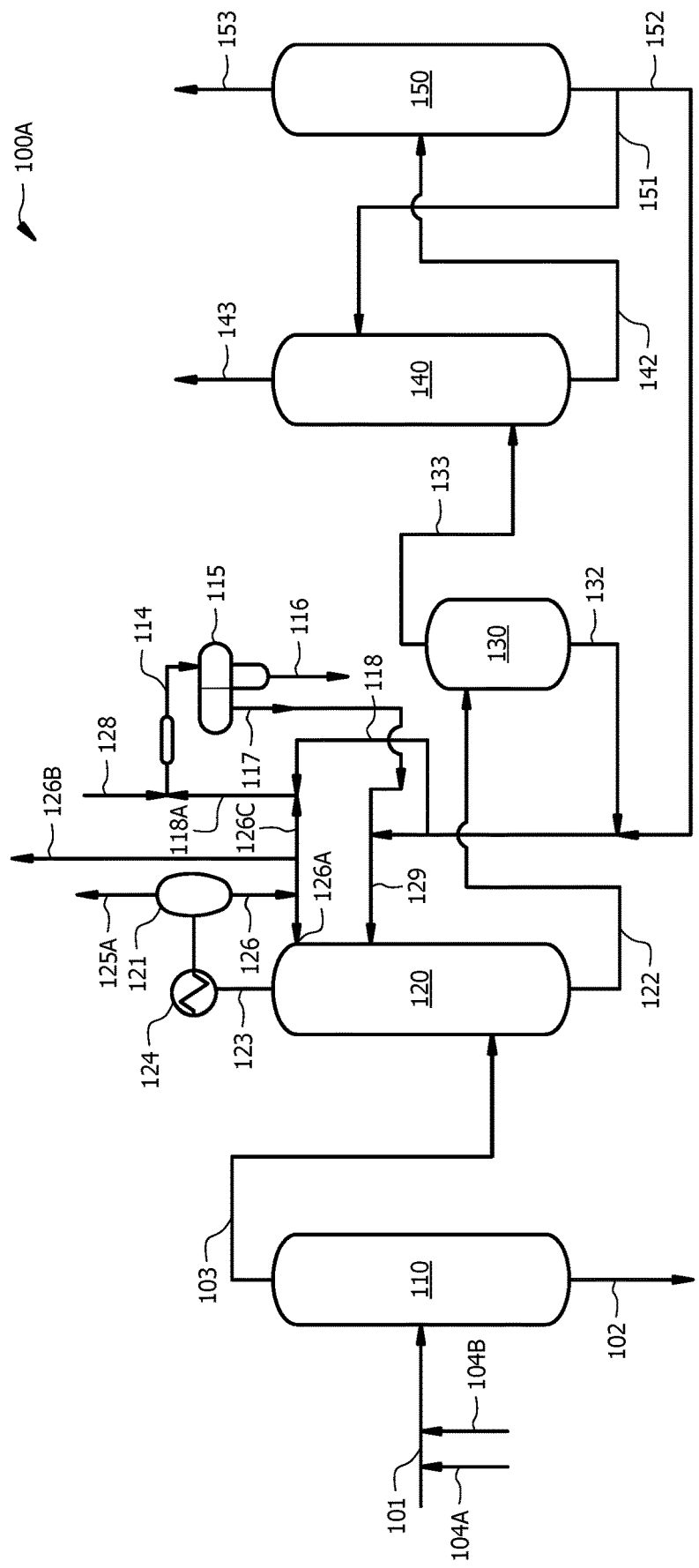
FIG. 2 is a schematic of a propylene oxide separation system 100A according to an embodiment of this disclosure.

FIG. 2 is a schematic of a propylene oxide separation system 100A according to another embodiment of this disclosure. In the embodiment of FIG. 2, side draw line 127 of the embodiment shown in FIG. 1 is replaced by line 126C. Line 126C can be configured such that a portion of the condensate from K/O 121 can be combined with decanter lean solvent line 118 in combined line 118A. Additionally, in the embodiment of FIG. 2, organic phase in organic phase outlet line 117 from decanter 115 can be directed to first extractive distillation column 120. In some implementations, organic phase in organic phase outlet line 117 can be combined with first extractive distillation column solvent in first extractive distillation column solvent inlet line 129 before entering first extractive distillation column 120.

Figure 3:
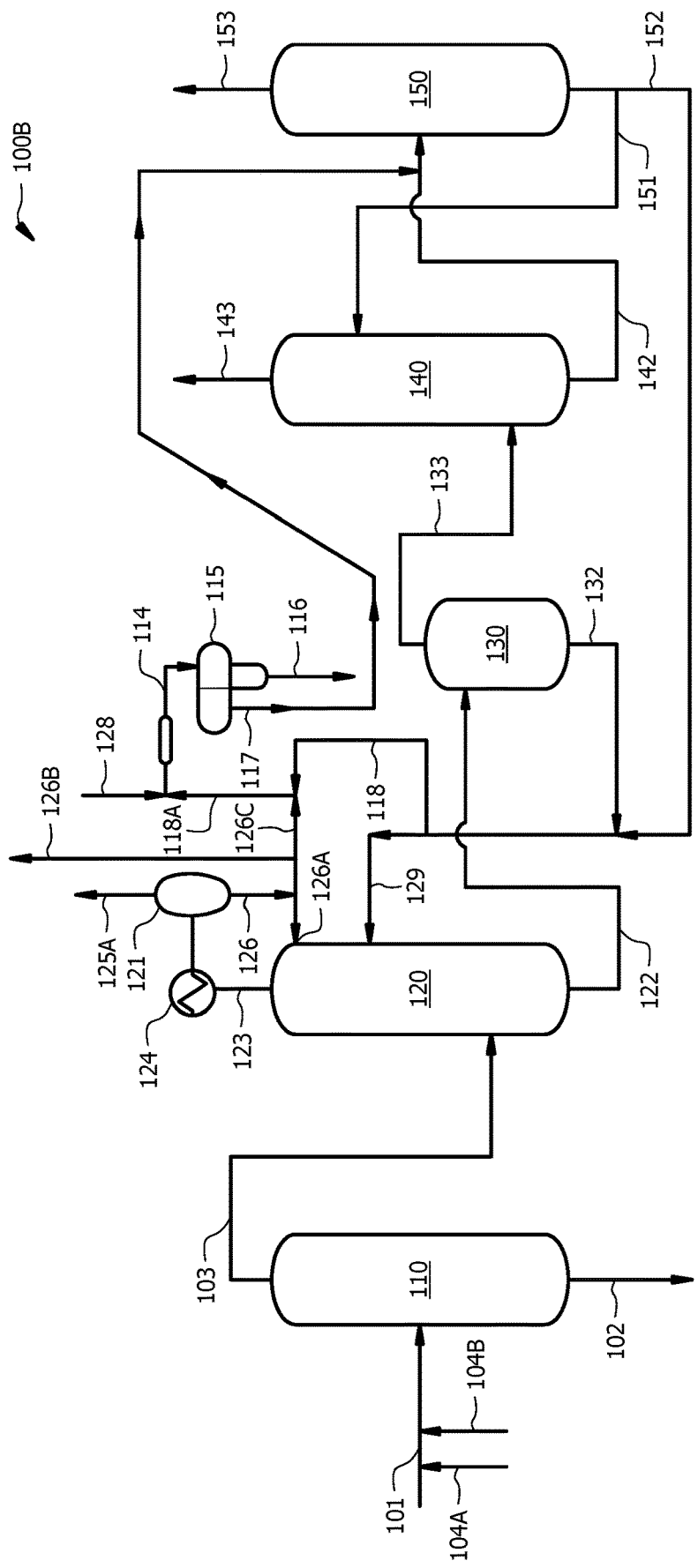
FIG. 3 is a schematic of a propylene oxide separation system 100B according to an embodiment of this disclosure.

FIG. 3 is a schematic of a propylene oxide separation system 100B according to another embodiment of this disclosure. In the embodiment of FIG. 3, side draw line 127 is similarly replaced by line 126C, whereby a portion of the condensate from K/O 121 can be combined with decanter lean solvent in decanter lean solvent line 118 in combined line 118A. In contrast to the embodiment of FIG. 2, in propylene oxide separation system 100B of FIG. 3, organic phase in organic phase outlet line 117 from decanter 115 can be directed to second solvent stripper 150. In embodiments, such as shown in FIG. 3, organic phase in organic phase outlet line 117 can be combined with second extractive distillation column bottoms in second extractive distillation column bottoms line 142 before entering second solvent stripper 150.

Figure 4:
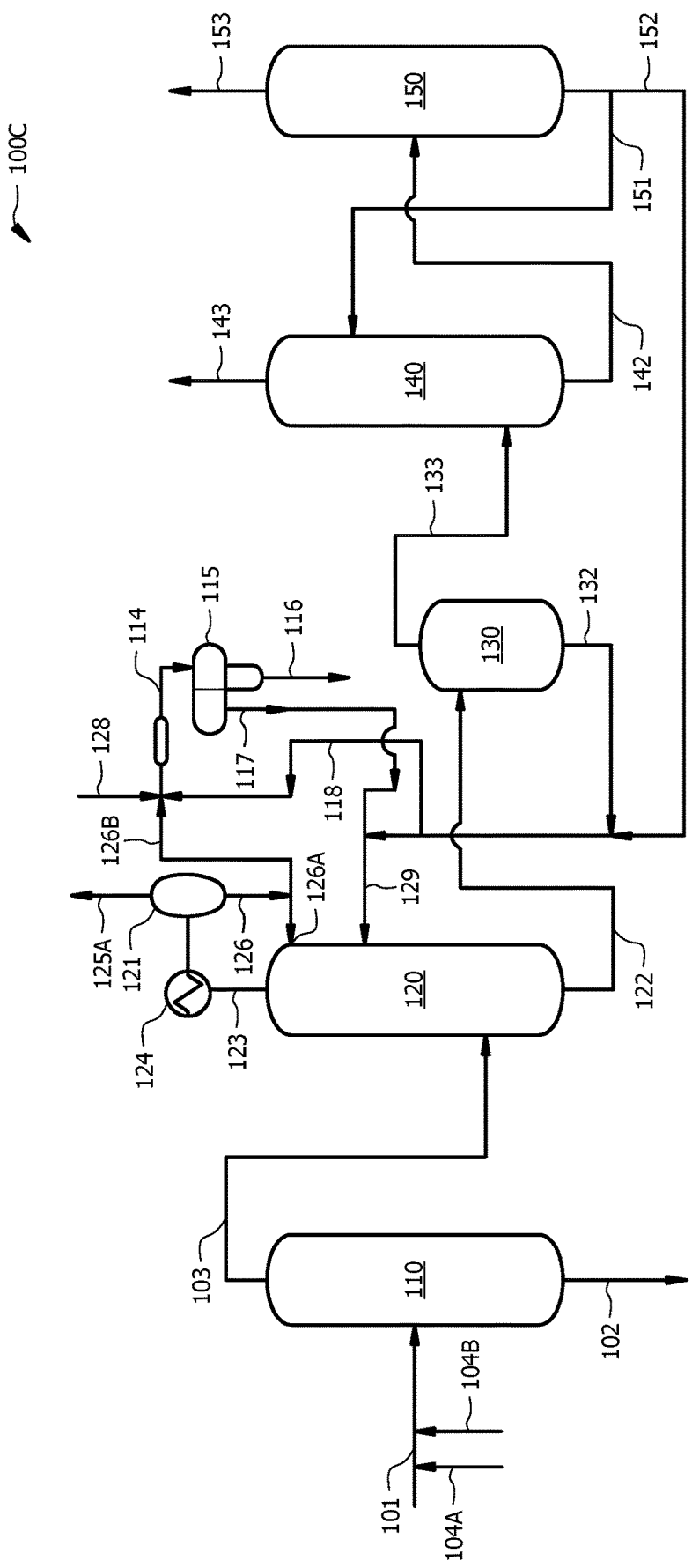
FIG. 4 is a schematic of a propylene oxide separation system 100C according to an embodiment of this disclosure.

FIG. 4 is a schematic of a propylene oxide separation system 100C according to another embodiment of this disclosure. In the embodiment of FIG. 4, liquid lights purge in liquid lights purge line 126B can be fed to decanter 115. In embodiments, liquid lights purge line 126B may be combined into decanter feed line 114 before being introduced to decanter 115. Additionally, in the embodiment of FIG. 4, organic phase in organic phase outlet line 117 from decanter 115 can be directed to first extractive distillation column 120. In embodiments, as shown in FIG. 4, organic phase in organic phase outlet line 117 can be combined with first extractive distillation column solvent into first extractive distillation column solvent inlet line 129 before entering first extractive distillation column 120.

Figure 5:
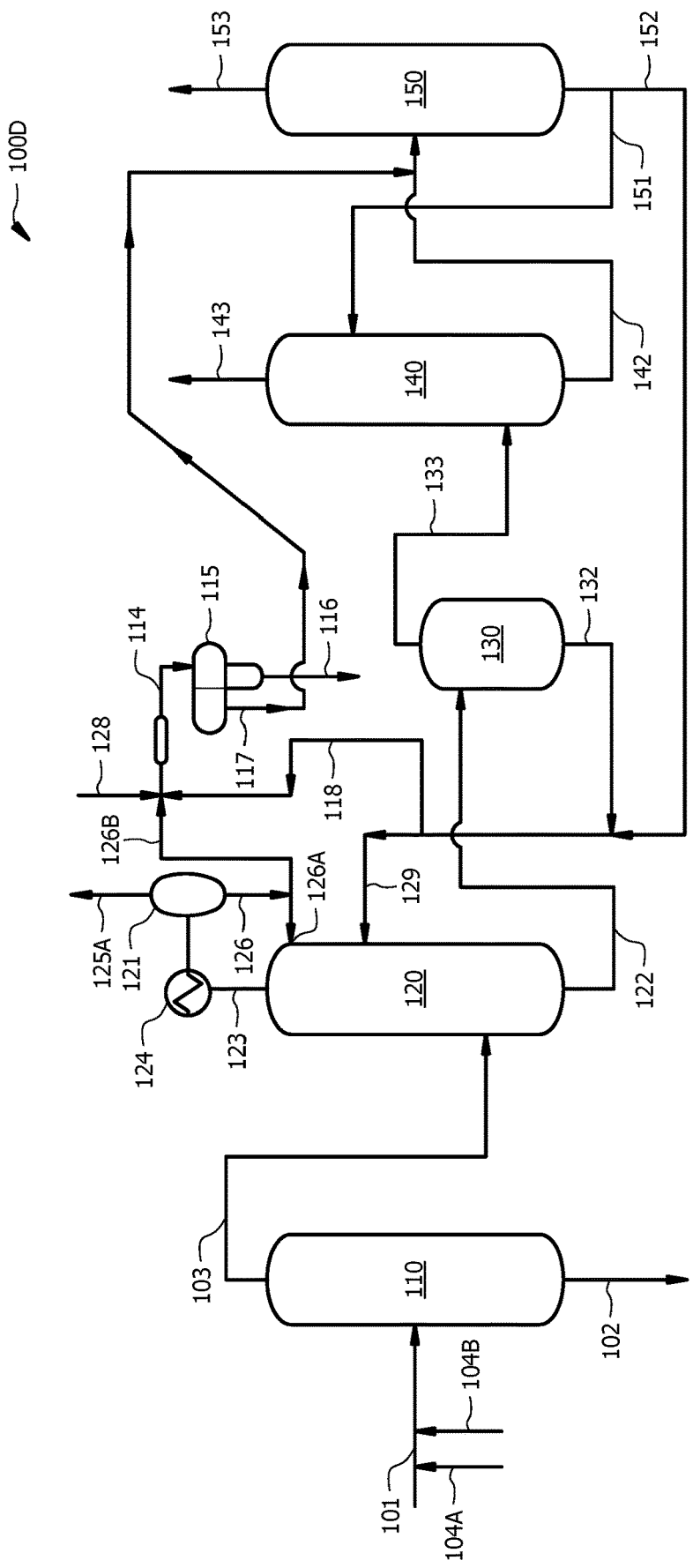
FIG. 5 is a schematic of a propylene oxide separation system 100D according to an embodiment of this disclosure.

FIG. 5 is a schematic of a propylene oxide separation system 100D according to another embodiment of this disclosure. In the embodiment of FIG. 5, liquid lights purge in liquid lights purge line 126B can be fed to decanter 115. In embodiments, liquid lights purge line in liquid lights purge line 126B may be combined into decanter feed line 114 before being introduced to decanter 115. Additionally, in the embodiment of FIG. 5, organic phase in organic phase outlet line 117 from decanter 115 can be directed to second solvent stripper 150. In embodiments, such as that in FIG. 5, organic phase in organic phase outlet line 117 can be combined with second extractive distillation column bottoms in second extractive distillation column bottoms line 142 before entering second solvent stripper 150.

Features/Potential Benefits

The system and method of this disclosure provide for heavies removal from a crude PO stream as an upstream step in a PO purification process. In embodiments, heavies removal is the first step in a PO purification process according to this disclosure. In embodiments, heavies removal via non-solvent distillation is the sole distillation step upstream of (a first) extractive distillation in a PO purification process according to this disclosure. In embodiments, a system of this disclosure comprises no non-solvent distillation column upstream of a first extractive distillation column other than the heavies distillation column. In embodiments, a method according to this disclosure comprises no non-solvent distillation upstream of the first extractive distillation, other than the heavies distillation column. In embodiments, downstream separations (e.g., a first extractive distillation column, a second extractive distillation column, or both) may be effected at lower temperatures than corresponding separations/units of a similar system absent the upstream heavies removal of this disclosure. In embodiments, a system of this disclosure comprises no caustic mixer and/or backwash column as described in U.S. Pat. No. 9,593,090.

In embodiments, the total PO purge, which is the total PO in the combined flows of (a) the heavies purge bottoms extracted from heavies distillation column 110 via heavies purge bottoms line 102, (b) the lights purge extracted from first extractive distillation column 120 via first extractive distillation column overhead vapor purge line 125A and liquid lights purge line 126B, (c) the light hydrocarbon purge stream extracted from second solvent stripper 150 via second solvent stripper overhead line 153, and (d) the aqueous phase purge extracted from decanter 115 via aqueous phase purge outlet line 116, comprise less than or equal to 18, 17, 16, 15, 14, 13, 12, 11, 10, 9, 8, 7, 6, 5, 4, 3, 2, 1, 0.5, or 0.3 weight percent of the total PO in the crude PO stream fed to heavies distillation column 110 (i.e., the total PO in the crude PO fed to heavies distillation column 110 via crude PO inlet line 101). In embodiments, the system or method of this disclosure is considered reduced slop PO, and the total PO purge is less than or equal to 18, 17.5, 17, 16.5, 16, 15.5, 15, 14.5, or 14 weight percent of the total PO in the crude PO stream. In embodiments, the system or method of this disclosure is considered lower slop PO, and the total PO purge is less than or equal to 8, 7, 6, 5, 4, 3, 2, 1, 0.5, 0.3, or 0.1 weight percent of the total PO in the crude PO stream.

By positioning a non-solvent heavies distillation column at the front of the PO purification and removing a heavies cut from the bottom thereof, a purer PO stream can be introduced into the subsequent extractive distillation column (e.g., first extractive distillation column 120). Unexpectedly, removal of a heavies cut (which may remove aldehydes and/or aldehyde derivatives such as, but not limited to, formaldehyde and formaldehyde derivatives) with the bottoms of the upfront heavies distillation column 110 can, in embodiments, result in more efficient lights removal (e.g., via lights purge overhead in first extractive distillation column overhead vapor purge line 125A and liquid lights purge line 126B) in an extractive distillation column downstream from the heavies distillation column (e.g., in first extractive distillation column 120). This may provide for facilitation of production of a purified PO product having a desired purity. In embodiments, the herein-disclosed system and method provide for removal of the purified PO product as an overhead/distillate cut from a downstream extractive distillation column (e.g., as overhead PO product stream in second extractive distillation column overhead line 143 from second extractive distillation column 140).

The herein-disclosed system and method comprising upstream heavies removal may provide for a decreased solvent flow in a front loop comprising first extractive distillation column 120 and first solvent stripper 130 relative to a conventional PO purification absent heavies removal upstream of (a first) extractive distillation to remove a lights purge. Such a decreased solvent flow may, in embodiments, comprise a reduction of at least 30, 40, or 50% in the volumetric flow rate of first solvent stripper bottoms line 132, for example.

Upstream heavies removal as per this disclosure may enable introduction of crude PO streams having relatively high amounts of water and methanol, for example, directly to the PO purification system 100 (e.g., directly to heavies distillation column 110).

The following examples merely illustrate the system and method of this disclosure. Those skilled in the art will recognize many variations that are within the spirit of this disclosure and the scope of the claims.

EXAMPLES

Example 1

Referring to FIG. 1, 3 lb/hr of crude PO was fed to heavies distillation column 110 at a point 15 to 25% up from the bottom thereof. Heavies distillation column 110 was built from 2-inch schedule 40 stainless steel pipe, and contained therein 195 inches of PRO-PAK® 0.24" stainless steel packing. The heavies distillation column pressure was maintained to a pressure of approximately 25 psig. Heat was applied to a reboiler at the bottom of heavies distillation column 110 in order to take approximately 90 to 95% of the feed overhead. The bottoms flow from heavies distillation column 110 was 0.195 lb/hr. The overhead vapors were condensed, and 4.5 lb/hr of the condensed liquid was returned to the top of heavies distillation column 110 as reflux.

The distillate from heavies distillation column 110 was fed to extractive distillation column 120 at a point at least 60% up from a bottom thereof. First extractive distillation column 120 was made of 2" schedule 40 stainless steel pipe, and contained therein 149 inches of PRO-PAK® 0.24" stainless steel packing. First extractive distillation column 120 was maintained at a pressure of between 25 and 30 psig. First extractive distillation column 120 had a liquid side draw from a hat tray, located approximately 80 to 85% of the way up the column from the bottom thereof. A pump was used to control the side draw at 0.45 lb/hr.

Side draw liquid was mixed with 2.2 lb/hr of lean solvent from the bottom of first solvent splitter 130 using a static mixer and introduced into a decanter 115. Decanter 115 was constructed of 2" inner diameter (ID) glass pipe. An amount of 0.02 lb/hr of aqueous phase was collected from the base of decanter 115 and discarded. The upper layer from decanter 115 was mixed with 10 lb/hr of lean solvent from the bottom of first solvent stripper 130 plus 1.3 lb/hr of lean solvent from the bottom of second solvent stripper 150 and pumped back into first extractive distillation column 120 at a point between 75% to 85% up from the bottom thereof. Vapor from the top of first extractive distillation column 120 was condensed. An amount of 0.15 lb/hr of the liquid condensate was taken as distillate. An amount of 0.57 lb/hr of liquid condensate was returned to the top of first extractive distillation column 120 as reflux. Sufficient heat was applied to the bottom of the first extractive distillation column 120 to generate enough vapor that the reflux drum level was held constant.

The bottoms from first extractive distillation column 120 was sent as feed to first solvent stripper 130 at the top thereof. First solvent stripper 130, which was made of 2" schedule 40 pipe, contained 21 inches of packing of the same type as heavies distillation column 110 and first extractive distillation column 120. Sufficient heat was applied to first solvent stripper 130 to take approximately 3.5 to 4.0 lb/hr of distillate. The bottoms of first solvent stripper 130 was used as lean solvent for first extractive distillation column 120 and decanter 115, as described hereinabove.

The overhead distillate from first solvent stripper 130 was condensed and pumped into second extractive distillation column 140 at a point 15 to 20% up from the bottom thereof. Second extractive distillation column 140 was made of 2" schedule 40 stainless steel pipe, and contained therein 116 inches of PRO-PAK® 0.24" stainless steel packing. Second extractive distillation column 140 was held at a pressure of approximately 20 to 25 psig. Second extractive distillation column 140 was also fed with 6.5 lb/hr of lean solvent from the bottom of second solvent stripper 150. This solvent was fed to second extractive distillation column 140 at a point 60 to 80% up from the bottom thereof. The vapor from the top of second extractive distillation column 140 was condensed, and 2.8 lb/hr of this liquid was fed to the top of second extractive distillation column 140 as reflux. The remainder of the condensed liquid was recovered as purified PO product.

The bottoms of second extractive distillation column 140 was fed to second solvent stripper 150 at a point 60 to 90% up from the bottom thereof. Second solvent stripper 150 was made of 2" schedule 40 stainless steel pipe, and contained therein 190 inches of PRO-PAK® 0.24" stainless steel packing. Second solvent stripper 150 was operated at a pressure of approximately 19 to 21 psig. The bottoms (lean solvent) from second solvent stripper 150 was divided between 1.3 lb/hr sent to first extractive distillation column 120 and 6.5 lb/hr sent to second extractive distillation column 140. The overhead vapor from second solvent stripper 150 was condensed. An amount of 1.2 lb/hr of condensed liquid was fed to the top of second solvent stripper 150 as reflux. An amount of 0.032 lb/hr of the condensed liquid was taken as distillate. The compositions and flow rates of the crude PO feed, the product PO, and the four purge or 'impurity' streams for this Example 1 are shown in Table 1 below.

TABLE 1

Data and Results from Example 1

| | Crude PO Feed (Line 101) | Heavies Distillation Column 110 Bottoms (Line 102) | First Extractive Distillation Column 120 Overhead (Lines 125A and 126B) | Decanter 115 Aqueous Phase (Line 116) | Second Extractive Distillation or 'PO Product' Column 140 Overhead (Line 143) | Second Solvent Stripper Column 150 Overhead (Line 153) |
|---|---|---|---|---|---|---|
| Propylene Oxide, wt % | 96.74 | 56.95 | 95.88 | 25.79 | 99.994 | 94.76 |
| Acetone, wt % | 2.13 | 34.2 | 0 | 0 | 0 | 0.0016 |
| Water, wt % | 0.50 | 4.38 | 0.115 | 39.6 | 0.0013 | 0.018 |
| Methanol, wt % | 0.295 | 1.19 | 1.80 | 28.53 | 0 | 0.0011 |
| Solvent, wt % | 0 | 0 | 0 | 0.221 | 0 | 2.76 |

TABLE 1-continued

Data and Results from Example 1

|  | Crude PO Feed (Line 101) | Heavies Distillation Column 110 Bottoms (Line 102) | First Extractive Distillation Column 120 Overhead (Lines 125A and 126B) | Decanter 115 Aqueous Phase (Line 116) | Second Extractive Distillation or 'PO Product' Column 140 Overhead (Line 143) | Second Solvent Stripper Column 150 Overhead (Line 153) |
|---|---|---|---|---|---|---|
| Methyl Formate, wt % | 0.063 | 0.0014 | 1.16 | 0.031 | 0.0012 | 0 |
| Formaldehyde and Derivatives Thereof, wt % | 0.0067 | 0.0934 | 0 | 0.063 | 0 | 0.0003 |
| 2-Methyl-Pentane, wt % | 0.0133 | 0.0722 | 0.0023 | 0 | 0 | 1.08 |
| Flow rate, lb/hr | 3.0 | 0.195 | 0.15 | 0.020 | 2.60 | 0.032 |

This example shows the recovery of about 97% of the propylene oxide in the crude PO feed as substantially pure propylene oxide product.

Example 2

Referring to FIG. 1, 3 lb/hr of crude PO was fed to heavies distillation column 110 at a point 15 to 25% up from the bottom thereof. Heavies distillation column 110 was built from 2-inch schedule 40 stainless steel pipe, and contained therein 195 inches of PRO-PAK® 0.24" stainless steel packing. The heavies distillation column pressure was maintained at a pressure of approximately 25 psig. Heat was applied to a reboiler at the bottom of heavies distillation column 110 in order to take approximately 93 to 99% of the feed overhead. The bottoms flow from heavies distillation column 110 was 0.095 lb/hr. The overhead vapors from heavies distillation column 110 were condensed, and 4.5 lb/hr of the condensed liquid was returned to the top of heavies distillation column 110 as reflux.

An amount of 2.9 lb/hr of distillate from heavies distillation column 110 was fed to first extractive distillation column 120 at a point at least 60% up from the bottom thereof. Second distillation column 120 was made of 2" schedule 40 stainless steel pipe, and contained therein 149 inches of PRO-PAK® 0.24" stainless steel packing. Second distillation column 120 was maintained at a pressure of between 25 and 30 psig. Second distillation column 120 had a liquid side draw from a hat tray, located approximately 80 to 85% of the way up the column from the bottom thereof. A pump was used to control the side draw at 0.45 lb/hr.

Side draw liquid was mixed with 2.2 lb/hr of lean solvent from the bottom of first solvent stripper 130 using a static mixer and then into a decanter 115. Decanter 115 was constructed of 2" ID glass pipe, mounted vertically. An amount of 0.02 lb/hr of aqueous phase was collected from the base of decanter 115 and discarded. The upper layer from decanter 115 was mixed with 10 lb/hr of lean solvent from the bottom of first solvent stripper 130 plus 1.4 lb/hr of lean solvent from the bottom of second solvent stripper 150 and pumped back into first extractive distillation column 120 at a point between 75 and 85% up from the bottom thereof. Vapor from the top of first extractive distillation column 120 was condensed. An amount of 0.012 lb/hr of the liquid condensate was taken as distillate. An amount of 0.57 lb/hr of liquid condensate was returned to the top of first extractive distillation column 120 as reflux. Sufficient heat was applied to the bottom of the first extractive distillation column 120 to generate enough vapor that the reflux drum level was held constant.

The bottoms from first extractive distillation column 120 was sent as feed to first solvent stripper 130 at the top thereof. First solvent stripper 130, which was made of 2" schedule 40 pipe, contained 21 inches of packing of the same type as heavies distillation column 110 and first extractive distillation column 120. Sufficient heat was applied to first solvent stripper 130 to take approximately 4.0 to 4.5 lb/hr of overhead. The bottoms of first solvent stripper 130 was used as lean solvent for first extractive distillation column 120 and decanter 115, as described hereinabove. The overhead vapor from first solvent stripper 130 was condensed and pumped into second extractive distillation column 140 at a point 15 to 20% up from the bottom thereof. Second extractive distillation column 140 was made of 2" schedule 40 stainless steel pipe, and contained therein 116 inches of PRO-PAK® 0.24" stainless steel packing. Second extractive distillation column 140 was held at a pressure of approximately 20 to 25 psig. Second extractive distillation column 140 was also fed with 6.5 lb/hr of lean solvent from the bottom of second solvent stripper 150. This solvent was fed to second extractive distillation column 140 at a point 60 to 90% up from the bottom thereof. The vapor from the top of second extractive distillation column 140 was condensed, and 2.7 lb/hr of this liquid was fed to the top of second extractive distillation column 140 as reflux. The remainder of the condensate (2.9 lb/hr) was recovered as purified PO product.

The bottoms of second extractive distillation column 140 was fed to second solvent stripper 150 at a point 60 to 90% up from the bottom thereof. Second solvent stripper 150 was made of 2" schedule 40 stainless steel pipe, and contained therein 190 inches of PRO-PAK® 0.24" stainless steel packing. Second solvent stripper 150 was operated at a pressure of approximately 19 to 21 psig. The bottoms (lean solvent) from second solvent stripper 150 was divided between 1.4 lb/hr sent to first extractive distillation column 120 and 6.5 lb/hr sent to second extractive distillation column 140. The overhead vapor from second solvent stripper 150 was condensed. An amount of 1.2 lb/hr of condensate was fed to the top of second solvent stripper 150 as reflux. An amount of 0.010 lb/hr of the condensate was taken as distillate. The compositions and flow rates of the crude PO feed, the product PO, and the four purge or 'impurity' streams for this Example 2 are shown in Table 2.

TABLE 2

Data and Results from Example 2

| | Crude PO Feed (Line 101) | Heavies Distillation Column 110 Bottoms (Line 102) | First Extractive Distillation Column 120 Overhead (Lines 125A and 126B) | Decanter 115 Aqueous Phase (Line 116) | Second Extractive Distillation or 'PO Product' Column 140 Overhead (Line 143) | Second Solvent Stripper Column 150 Overhead (Line 153) |
|---|---|---|---|---|---|---|
| Propylene oxide, wt % | 96.62 | 15.29 | 88.51 | 30.53 | 99.984 | 89.64 |
| Acetone, wt % | 2.22 | 68.13 | 0 | 0.0001 | 0 | 0.0041 |
| Water, wt % | 0.507 | 7.64 | 0.0644 | 31.1 | 0.010 | 0.070 |
| Methanol, wt % | 0.290 | 1.26 | 1.60 | 33.93 | 0 | 0.0061 |
| Solvent, wt % | 0 | 0 | 0 | 1.71 | 0 | 4.41 |
| Methyl Formate, wt % | 0.056 | 0.0003 | 5.42 | 0.0646 | 0.0026 | 0.0009 |
| Formaldehyde and Formaldehyde Derivatives, wt % | 0.0072 | 0.184 | 0 | 0.0443 | 0 | 0.0004 |
| 2-Methyl-Pentane, wt % | 0.0113 | 0.127 | 0.0027 | 0 | 0 | 2.22 |
| Flow rate, lb/hr | 3.0 | 0.095 | 0.012 | 0.017 | 2.87 | 0.0102 |

This example shows the recovery of about 97% of the propylene oxide in the crude as pure propylene oxide product.

ADDITIONAL DISCLOSURE

The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and such variations are considered within the scope and spirit of the present disclosure. Alternative embodiments that result from combining, integrating, and/or omitting features of the embodiment(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

Embodiments disclosed herein include:

A: A propylene oxide separation system comprising: a heavies distillation column configured to receive a crude propylene oxide stream and discharge a heavies purge bottoms comprising at least one impurity selected from acetone, methanol, aldehydes, aldehyde derivatives, water, heavy hydrocarbons comprising $C_5+$, or combinations thereof, and discharge a heavies distillation column overhead stream comprising a majority of the propylene oxide entering with the crude propylene oxide stream; and a first extractive distillation column configured to receive the heavies distillation column overhead stream and a first extraction solvent stream comprising a hydrocarbon solvent, and discharge a lights purge overhead comprising at least one impurity selected from aldehydes (for example, acetaldehyde, formaldehyde, etc.), methyl formate, methanol, water, $C_3$ hydrocarbons, $C_4$ hydrocarbons or combinations thereof, and discharge a rich solvent bottoms stream comprising a majority of the propylene oxide entering via the heavies distillation column overhead stream.

B: A method comprising: (i) subjecting a crude propylene oxide stream to non-solvent distillation in a heavies distillation column to produce a heavies purge bottoms comprising at least one impurity selected from acetone, methanol, aldehydes, aldehyde derivatives, water, heavy hydrocarbons comprising $C_5+$, or combinations thereof, and a heavies distillation column overhead stream comprising a majority of the propylene oxide entering in the crude propylene oxide stream; (ii) introducing the heavies distillation column overhead stream and a first extractive distillation solvent stream comprising a hydrocarbon solvent into a first extractive distillation column to produce a lights purge overhead comprising at least one impurity selected from aldehydes (for example, acetaldehyde, formaldehyde, etc.), methyl formate, methanol, water, $C_3$ hydrocarbons, $C_4$ hydrocarbons, or combinations thereof, and a rich solvent bottoms stream comprising a majority of the propylene oxide entering via the heavies distillation column overhead stream; (iii) introducing a side draw from the first extractive distillation column into a decanting apparatus, and therein allowing the formation of an aqueous phase purge comprising water and methanol, aldehydes (for example, acetaldehyde, formaldehyde, etc.), one or more glycols, or a combination thereof, and an organic phase stream comprising propylene oxide and the hydrocarbon solvent; and (iv) introducing the rich solvent bottoms stream from the first extractive distillation column into a first solvent stripper to produce a first solvent stripper overhead comprising a majority of the propylene oxide entering the first solvent stripper via the rich solvent bottoms stream and a first solvent stripper bottoms comprising lean hydrocarbon solvent.

C: A method comprising: (i) subjecting a crude propylene oxide stream to non-solvent distillation in a heavies distillation column to produce a heavies purge bottoms comprising at least one impurity selected from acetone, methanol, aldehydes, aldehyde derivatives, water, heavy hydrocarbons comprising $C_5+$, or combinations thereof, and a heavies distillation column overhead stream comprising a majority of the propylene oxide entering in the crude propylene oxide stream; (ii) introducing the heavies distillation column overhead stream and a first extractive distillation solvent stream comprising a hydrocarbon solvent into a first extractive distillation column to produce a lights purge overhead comprising at least one impurity selected from aldehydes (for example, acetaldehyde, formaldehyde, etc.), methyl formate, methanol, water, C3 hydrocarbons, C4 hydrocarbons, or combinations thereof, and a rich solvent bottoms stream comprising a majority of the propylene oxide entering via the heavies distillation column overhead stream; (iii) introducing at least a portion of the lights purge overhead from the first extractive distillation column into a decanting apparatus, and therein allowing the formation of an aqueous phase purge comprising water and methanol, one or more glycols, or a combination thereof, and an organic phase stream comprising propylene oxide and the hydrocarbon solvent; and (iv) introducing the rich solvent bottoms stream from the first extractive distillation column into a first solvent stripper to produce a first solvent stripper overhead comprising a majority of the propylene oxide entering the first solvent stripper via the rich solvent bottoms stream and a first solvent stripper bottoms comprising lean hydrocarbon solvent.

Each of embodiments A, B and C may have one or more of the following additional elements:

Element 1: further comprising one or more feed lines configured to introduce methanol, water, or both into the crude propylene oxide stream based on a total aldehyde concentration in the heavies distillation column overhead stream. Element 2: wherein the first extractive distillation column is further configured to discharge a side draw, and wherein the propylene oxide separation system further comprises a decanter configured to receive the side draw, a lean hydrocarbon solvent stream comprising the hydrocarbon solvent, and optionally water, allow formation of an aqueous phase and an organic phase, discharge an aqueous phase purge comprising water and methanol, aldehydes (for example, acetaldehyde, formaldehyde, etc.), one or more glycols, or a combination thereof, and discharge an organic phase stream comprising propylene oxide and the hydrocarbon solvent. Element 3: wherein the decanter is fluidly connected with the first extractive distillation column, whereby the organic phase from the decanter can be introduced into the first extractive distillation column. Element 4: further comprising a first solvent stripper configured to receive the rich solvent bottoms stream from the first extractive distillation column, discharge a first solvent stripper overhead comprising a majority of the propylene oxide entering with the rich solvent bottoms stream, and discharge a first solvent stripper bottoms comprising lean hydrocarbon solvent. Element 5: wherein the first extractive distillation column is fluidly connected with the first solvent stripper, whereby at least a portion of the lean hydrocarbon solvent from the first solvent stripper bottoms can be introduced into the first extractive distillation column via the first extraction solvent stream. Element 6: further comprising a second extractive distillation column configured to receive the first solvent stripper overhead and a second extraction solvent stream comprising the hydrocarbon solvent, discharge an overhead propylene oxide product stream comprising a majority of the propylene oxide from the first solvent stripper overhead, and discharge a second extractive distillation column bottoms comprising rich hydrocarbon solvent; and a second solvent stripper configured to receive the second extractive distillation column bottoms, discharge a hydrocarbon purge overhead stream, and discharge a second solvent stripper bottoms comprising lean hydrocarbon solvent. Element 7: wherein the second solvent stripper is fluidly connected with the first extractive distillation column, the decanter, or both, whereby a portion of the lean hydrocarbon solvent from the second solvent stripper bottoms can be introduced into the first extractive distillation column, the decanter, or both. Element 8: wherein the second solvent stripper is fluidly connected with the second extractive distillation column, whereby at least a portion of the lean hydrocarbon solvent from the second solvent stripper bottoms can be introduced into the second extractive distillation column via the second extraction solvent stream. Element 9: operable to provide an overhead propylene oxide product stream comprising less than 0.010 wt % methanol, less than 0.010 wt % methyl formate, less than 0.025 wt % water, or a combination thereof, from a crude propylene oxide stream comprising from 0.05 to 1.5 wt % methanol, from 0.05 to 1.5 wt % methyl formate, from 0.05 to 1.5 wt % water, or a combination thereof, respectively. Element 10: wherein the hydrocarbon solvent comprises one or more $C_8$-$C_{20}$ paraffins. Element 11: wherein the first extractive distillation column, the second extractive distillation column, or a combination thereof, is operable at a lower temperature than a corresponding propylene oxide separation system that does not comprise a heavies distillation column as the first column which receives the crude propylene oxide stream, that does not comprise a heavies distillation column as the sole non-solvent distillation column which receives the crude propylene oxide stream upstream of the first extractive distillation column, or both. Element 12: operable to produce an overhead propylene oxide product stream having a propylene oxide purity of greater than or equal to 99.0, 99.9, or 99.99 wt. % propylene oxide. Element 13: wherein an amount of propylene oxide in the combined flows of: (a) the heavies purge bottoms from the heavies distillation column; (b) the lights purge overhead from the first extractive distillation column; (c) the hydrocarbon purge overhead stream from the second solvent stripper; and (d) the aqueous phase purge from the decanter comprises less than 18 weight percent of the total propylene oxide in the crude propylene oxide stream fed to the heavies distillation column. Element 14: wherein an amount of propylene oxide in the combined flows of: (a) the heavies purge bottoms from the heavies distillation column; (b) the lights purge overhead from the first extractive distillation column; (c) the hydrocarbon purge overhead stream from the second solvent stripper; and (d) the aqueous phase purge from the decanter comprises less than 3 weight percent of the total propylene oxide in the crude propylene oxide stream fed to the heavies distillation column. Element 15: comprising no non-solvent distillation column upstream of the first extractive distillation column other than the heavies distillation column. Element 16: wherein the crude propylene oxide stream is from a propylene oxide/tert-butanol (PO/TBA) process. Element 17: wherein the aldehyde comprises or is formaldehyde. Element 18: further comprising: a decanter configured to receive at least a portion of the lights purge overhead, a lean hydrocarbon solvent stream comprising the hydrocarbon solvent, and optionally water, allow formation of an aqueous phase and an organic phase, and discharges an aqueous phase purge comprising water and methanol, one or more glycols, or a combination thereof, and discharge an organic phase stream comprising propylene oxide and the hydrocarbon solvent back to the first extractive distillation column. Element 19: further comprising: a decanter configured to receive at least a portion of the lights purge overhead, a lean hydrocarbon solvent stream comprising the hydrocarbon solvent, and optionally water, allow formation of an aqueous phase and an organic phase, discharge an aqueous phase purge comprising water and methanol, one or more glycols, or a combination thereof, and discharge an organic phase stream comprising propylene oxide and the hydrocarbon solvent; and a solvent stripper configured to receive the organic phase stream from the decanter, discharge a hydrocarbon purge overhead stream comprising at least a portion of the propylene oxide from the organic phase stream, and discharge a solvent stripper bottoms comprising lean hydrocarbon solvent. Element 20: further comprising feeding a portion of the first solvent stripper bottoms comprising lean hydrocarbon solvent into the first extractive distillation column and another portion of the first solvent stripper bottoms comprising lean hydrocarbon solvent to the decanting apparatus. Element 21: wherein the heavies purge bottoms comprises at least 10% of an amount of methanol introduced with the crude propylene oxide stream, at least 40% of an amount of water introduced with the crude propylene oxide stream, or both. Element 22: further comprising introducing the organic phase stream from the decanting apparatus to the first extractive distillation column. Element 23: further comprising: (v) subjecting the first solvent stripper overhead to extractive distillation by introducing the first solvent stripper overhead and a second extractive distillation solvent stream comprising the hydrocarbon solvent into a second extractive distillation column, thus producing a purified propylene oxide product as an overhead stream and a second extractive distillation column bottoms comprising rich hydrocarbon solvent; (vi) introducing the second extractive distillation column bottoms comprising rich hydrocarbon solvent into a second solvent stripper to produce a light hydrocarbon overhead purge stream and a second solvent stripper bottoms comprising lean hydrocarbon solvent; and (vii) introducing at least a portion of the second solvent stripper bottoms into the second extractive distillation column, the first extractive distillation column, the decanting apparatus, or a combination thereof. Element 24: wherein an amount of propylene oxide in the combined flows of: (a) the heavies purge bottoms from the heavies distillation column; (b) the lights purge overhead from the first extractive distillation column; (c) the light hydrocarbon overhead purge stream from the second solvent stripper; and (d) the aqueous phase purge from the decanting apparatus comprises less than 18 weight percent of the total propylene oxide in the crude propylene oxide stream. Element 25: wherein an amount of propylene oxide in the combined flows of: (a) the heavies purge bottoms from the heavies distillation column; (b) the lights purge overhead from the first extractive distillation column; (c) the light hydrocarbon overhead purge stream from the second solvent stripper; and (d) the aqueous phase purge from the decanting apparatus comprises less than 3 weight percent of the total propylene oxide in the crude propylene oxide stream. Element 26: wherein the purified propylene oxide product has a propylene oxide purity of greater than or equal to 99.0, 99.9, or 99.99 wt. % propylene oxide. Element 27: wherein the second extractive distillation column is operated at a pressure in the range of from 0 to 60 psig (0 to 414 kPa gauge), at a temperature in the range of from 30 to 200 degrees Celsius, or both. Element 28: wherein the second extractive distillation column is operated at a pressure in the range of from 10 to 30 psig (69 to 207 kPa gauge). Element 29: wherein the second extractive distillation column is operated at a temperature in the range of from 40 to 185 degrees Celsius. Element 30: wherein the heavies distillation column is operated at a pressure in the range of from 0 to 60 psig (0 to 414 kPa gauge), at a temperature in the range of from 30 to 150 degrees Celsius, or both; wherein the first extractive distillation column is operated at a pressure in a range of 0 to 60 psig (0 to 414 kPa gauge), at a temperature in the range of 30 to 200 degrees Celsius, or both; or a combination thereof. Element 31: wherein the heavies distillation column is operated at a pressure in the range of from 10 to 30 psig (69 to 207 kPa gauge). Element 32: wherein the first extractive distillation column is operated at a pressure in the range of from 10 to 30 psig (69 to 207 kPa gauge). Element 33: wherein the heavies distillation column is operated at a temperature in the range of from 50 to 100 degrees Celsius. Element 34: wherein the first extractive distillation column is operated at a temperature in the range of from 50 to 115 degrees Celsius. Element 35: wherein the crude propylene oxide stream is an effluent stream from a propylene oxide/tert-butanol (PO/TBA) process. Element 36: wherein the heavies distillation column is operated at a pressure in the range of from 0 to 60 psig (0 to 414 kPa gauge), at a temperature in the range of from 30 to 150 degrees Celsius, or both; wherein the first extractive distillation column is operated at a pressure in a range of 0 to 60 psig (0 to 414 kPa gauge), at a temperature in the range of 30 to 200 degrees Celsius, or both; wherein the second extractive distillation column is operated at a pressure in the range of from 0 to 60 psig (0 to 414 kPa gauge), at a temperature in the range of from 30 to 200 degrees Celsius, or both; or a combination thereof. Element 37: wherein the first extractive distillation column receives at least a portion of the organic phase stream from the decanting apparatus. Element 38: wherein a solvent stripper receives at least a portion of the organic phase from the decanting apparatus. Element 29: wherein an amount of propylene oxide in the combined flows of: (a) the heavies purge bottoms from the heavies distillation column; (b) the lights purge overhead from the first extractive distillation column; (c) the hydrocarbon purge overhead stream from the second solvent stripper; and (d) the aqueous phase purge from the decanter comprises from 1 to 18 weight percent of the total propylene oxide in the crude propylene oxide stream fed to the heavies distillation column.

While certain embodiments have been shown and described, modifications thereof can be made by one skilled in the art without departing from the teachings of this disclosure.

Numerous other modifications, equivalents, and alternatives, will become apparent to those skilled in the art once the above disclosure is fully appreciated. It is intended that the following claims be interpreted to embrace such modifications, equivalents, and alternatives where applicable. Accordingly, the scope of protection is not limited by the description set out above but is only limited by the claims which follow, that scope including equivalents of the subject matter of the claims.

What is claimed is:

1. A propylene oxide separation system comprising:
   A) a heavies distillation column configured to receive a crude propylene oxide stream and discharge:
      a1) a heavies purge bottoms comprising at least one impurity selected from acetone, methanol, aldehydes, aldehyde derivatives, water, heavy hydrocarbons comprising $C_5+$, or combinations thereof, and
      a2) a heavies distillation column overhead stream comprising a majority of the propylene oxide entering with the crude propylene oxide stream; and
   B) a first extractive distillation column configured to receive the heavies distillation column overhead stream and a first extraction solvent stream comprising a hydrocarbon solvent, and discharge:
      b1) a lights purge overhead comprising at least one impurity selected from acetaldehyde, methyl formate, methanol, water, C3 hydrocarbons, C4 hydrocarbons, or combinations thereof, and
      b2) a rich solvent bottoms stream comprising a majority of the propylene oxide entering via the heavies distillation column overhead stream.

2. The propylene oxide separation system of claim 1, wherein the first extractive distillation column is further configured to discharge a side draw, and wherein the propylene oxide separation system further comprises a decanter configured to receive the side draw, a lean hydrocarbon solvent stream comprising the hydrocarbon solvent, and optionally water, allow formation of an aqueous phase and an organic phase, discharge an aqueous phase purge comprising water and methanol, one or more glycols, or a combination thereof, and discharge an organic phase stream comprising propylene oxide and the hydrocarbon solvent.

3. The propylene oxide separation system of claim 2 further comprising a first solvent stripper configured to receive the rich solvent bottoms stream from the first extractive distillation column, discharge a first solvent stripper overhead comprising a majority of the propylene oxide entering with the rich solvent bottoms stream, and discharge a first solvent stripper bottoms comprising lean hydrocarbon solvent.

4. The propylene oxide separation system of claim 3, wherein the first extractive distillation column is fluidly connected with the first solvent stripper, whereby at least a portion of the lean hydrocarbon solvent from the first solvent stripper bottoms can be introduced into the first extractive distillation column via the first extraction solvent stream.

5. The propylene oxide separation system of claim 3 further comprising:
   a second extractive distillation column configured to receive the first solvent stripper overhead and a second extraction solvent stream comprising the hydrocarbon solvent, discharge an overhead propylene oxide product stream comprising a majority of the propylene oxide from the first solvent stripper overhead, and discharge a second extractive distillation column bottoms comprising rich hydrocarbon solvent; and
   a second solvent stripper configured to receive the second extractive distillation column bottoms, discharge a hydrocarbon purge overhead stream, and discharge a second solvent stripper bottoms comprising lean hydrocarbon solvent.

6. The propylene oxide separation system of claim 5, wherein the second solvent stripper is fluidly connected with the first extractive distillation column, the decanter or both, whereby a portion of the lean hydrocarbon solvent from the second solvent stripper bottoms can be introduced into the first extractive distillation column, the decanter, or both.

7. The propylene oxide separation system of claim 5, wherein the second solvent stripper is fluidly connected with the second extractive distillation column, whereby at least a portion of the lean hydrocarbon solvent from the second solvent stripper bottoms can be introduced into the second extractive distillation column via the second extraction solvent stream.

8. The propylene oxide separation system of claim 1 comprising no non-solvent distillation column upstream of the first extractive distillation column other than the heavies distillation column.

9. The propylene oxide separation system of claim 1 further comprising:
   a decanter configured to receive at least a portion of the lights purge overhead, a lean hydrocarbon solvent stream comprising the hydrocarbon solvent, and optionally water, allow formation of an aqueous phase and an organic phase, discharges an aqueous phase purge comprising water and methanol, one or more glycols, or a combination thereof, and discharge an organic phase stream comprising propylene oxide and the hydrocarbon solvent back to the first extractive distillation column.

10. The propylene oxide separation system of claim 1 further comprising:
    a decanter configured to receive at least a portion of the lights purge overhead, a lean hydrocarbon solvent stream comprising the hydrocarbon solvent, and optionally water, allow formation of an aqueous phase and an organic phase, discharge an aqueous phase purge comprising water and methanol, one or more glycols, or a combination thereof, and discharge an organic phase stream comprising propylene oxide and the hydrocarbon solvent; and
    a solvent stripper configured to receive the organic phase stream from the decanter, discharge a hydrocarbon purge overhead stream comprising at least a portion of the propylene oxide from the organic phase stream, and discharge a solvent stripper bottoms comprising lean hydrocarbon solvent.

11. A method comprising:
    (i) subjecting a crude propylene oxide stream to non-solvent distillation in a heavies distillation column to produce a heavies purge bottoms comprising at least one impurity selected from acetone, methanol, aldehydes, aldehyde derivatives, water, heavy hydrocarbons comprising $C_5+$, or combinations thereof, and a heavies distillation column overhead stream comprising a majority of the propylene oxide entering in the crude propylene oxide stream;
    (ii) introducing the heavies distillation column overhead stream and a first extractive distillation solvent stream comprising a hydrocarbon solvent into a first extractive distillation column to produce a lights purge overhead comprising at least one impurity selected from acetaldehyde, methyl formate, methanol, water, C3 hydrocarbons, C4 hydrocarbons, or combinations thereof, and a rich solvent bottoms stream comprising a majority of the propylene oxide entering via the heavies distillation column overhead stream;
    (iii) introducing a side draw from the first extractive distillation column into a decanting apparatus, and therein allowing the formation of an aqueous phase purge comprising water and methanol, one or more glycols, or a combination thereof, and an organic phase stream comprising propylene oxide and the hydrocarbon solvent; and (iv) introducing the rich solvent bottoms stream from the first extractive distillation column into a first solvent stripper to produce a first solvent stripper overhead comprising a majority of the propylene oxide entering the first solvent stripper via the rich solvent bottoms stream and a first solvent stripper bottoms comprising lean hydrocarbon solvent.

12. The method of claim 11 further comprising feeding a portion of the first solvent stripper bottoms comprising lean hydrocarbon solvent into the first extractive distillation column and another portion of the first solvent stripper bottoms comprising lean hydrocarbon solvent to the decanting apparatus.

13. The method of claim 11, wherein the heavies purge bottoms comprises at least 10 wt % of an amount of methanol introduced with the crude propylene oxide stream, at least 40 wt % of an amount of water introduced with the crude propylene oxide stream, or both.

14. The method of claim 11 further comprising:

(v) subjecting the first solvent stripper overhead to extractive distillation by introducing the first solvent stripper overhead and a second extractive distillation solvent stream comprising the hydrocarbon solvent into a second extractive distillation column, thus producing a purified propylene oxide product as an overhead stream and a second extractive distillation column bottoms comprising rich hydrocarbon solvent;

(vi) introducing the second extractive distillation column bottoms comprising rich hydrocarbon solvent into a second solvent stripper to produce a light hydrocarbon overhead purge stream and a second solvent stripper bottoms comprising lean hydrocarbon solvent; and (vii) introducing at least a portion of the second solvent stripper bottoms into the second extractive distillation column, the first extractive distillation column, the decanting apparatus, or a combination thereof.

15. The method of claim 14, wherein the heavies distillation column is operated at a pressure in the range of from 0 to 60 psig (0 to 414 kPa gauge), at a temperature in the range of from 30 to 150 degrees Celsius, or both; wherein the first extractive distillation column is operated at a pressure in a range of 0 to 60 psig (0 to 414 kPa gauge), at a temperature in the range of 30 to 200 degrees Celsius, or both; wherein the second extractive distillation column is operated at a pressure in the range of from 0 to 60 psig (0 to 414 kPa gauge), at a temperature in the range of from 30 to 200 degrees Celsius, or both; or a combination thereof.

16. A method comprising:

(i) subjecting a crude propylene oxide stream to non-solvent distillation in a heavies distillation column to produce a heavies purge bottoms comprising at least one impurity selected from acetone, methanol, aldehydes, aldehyde derivatives, water, heavy hydrocarbons comprising $C_5+$, or combinations thereof, and a heavies distillation column overhead stream comprising a majority of the propylene oxide entering in the crude propylene oxide stream;

(ii) introducing the heavies distillation column overhead stream and a first extractive distillation solvent stream comprising a hydrocarbon solvent into a first extractive distillation column to produce a lights purge overhead comprising at least one impurity selected from acetaldehyde, methyl formate, methanol, water, C3 hydrocarbons, C4 hydrocarbons, or combinations thereof, and a rich solvent bottoms stream comprising a majority of the propylene oxide entering via the heavies distillation column overhead stream;

(iii) introducing at least a portion of the lights purge overhead from the first extractive distillation column into a decanting apparatus, and therein allowing the formation of an aqueous phase purge comprising water and methanol, one or more glycols, or a combination thereof, and an organic phase stream comprising propylene oxide and the hydrocarbon solvent; and (iv) introducing the rich solvent bottoms stream from the first extractive distillation column into a first solvent stripper to produce a first solvent stripper overhead comprising a majority of the propylene oxide entering the first solvent stripper via the rich solvent bottoms stream and a first solvent stripper bottoms comprising lean hydrocarbon solvent.

17. The method of claim 16 further comprising feeding a portion of the first solvent stripper bottoms comprising lean hydrocarbon solvent into the first extractive distillation column and another portion of the first solvent stripper bottoms comprising lean hydrocarbon solvent to the decanting apparatus.

18. The method of claim 16, wherein the heavies purge bottoms comprises at least 10 wt % of an amount of methanol introduced with the crude propylene oxide stream, at least 40 wt % of an amount of water introduced with the crude propylene oxide stream, or both.

19. The method of claim 16 further comprising:

(v) subjecting the first solvent stripper overhead to extractive distillation by introducing the first solvent stripper overhead and a second extractive distillation solvent stream comprising the hydrocarbon solvent into a second extractive distillation column, thus producing a purified propylene oxide product as an overhead stream and a second extractive distillation column bottoms comprising rich hydrocarbon solvent;

(vi) introducing the second extractive distillation column bottoms comprising rich hydrocarbon solvent into a second solvent stripper to produce a light hydrocarbon overhead purge stream and a second solvent stripper bottoms comprising lean hydrocarbon solvent; and (vii) introducing at least a portion of the second solvent stripper bottoms into the second extractive distillation column, the first extractive distillation column, the decanting apparatus, or a combination thereof.

20. The method of claim 19, wherein the heavies distillation column is operated at a pressure in the range of from 0 to 60 psig (0 to 414 kPa gauge), at a temperature in the range of from 30 to 150 degrees Celsius, or both; wherein the first extractive distillation column is operated at a pressure in a range of 0 to 60 psig (0 to 414 kPa gauge), at a temperature in the range of 30 to 200 degrees Celsius, or both; wherein the second extractive distillation column is operated at a pressure in the range of from 0 to 60 psig (0 to 414 kPa gauge), at a temperature in the range of from 30 to 200 degrees Celsius, or both; or a combination thereof.

* * * * *

UNITED STATES PATENT AND TRADEMARK OFFICE
CERTIFICATE OF CORRECTION

PATENT NO. : 10,513,502 B2
APPLICATION NO. : 16/267526
DATED : December 24, 2019
INVENTOR(S) : Ross-Medgaarden et al.

It is certified that error appears in the above-identified patent and that said Letters Patent is hereby corrected as shown below:

In the Specification

In Column 9, Line 3, delete "addition" and insert -- additional --, therefor
In Column 25, Line 22, delete "C3" and insert -- $C_3$ --, therefor
In Column 25, Line 22, delete "C4" and insert -- $C_4$ --, therefor In the Claims In Column 29, Claim 1, Line 21, delete "C3" and insert -- $C_3$ --, therefor
In Column 29, Claim 1, Line 21, delete "C4" and insert -- $C_4$ --, therefor
In Column 30, Claim 11, Line 60, delete "C3" and insert -- $C_3$ --, therefor
In Column 30, Claim 11, Line 61, delete "C4" and insert -- $C_4$ --, therefor
In Column 32, Claim 16, Line 4, delete "C3" and insert -- $C_3$ --, therefor
In Column 32, Claim 16, Line 5, delete "C4" and insert -- $C_4$ --, therefor Signed and Sealed this
Nineteenth Day of July, 2022

Katherine Kelly Vidal
*Director of the United States Patent and Trademark Office*